(12) United States Patent
Battersby et al.

(10) Patent No.: US 9,695,416 B2
(45) Date of Patent: Jul. 4, 2017

(54) METHOD OF NORMALIZING BIOLOGICAL SAMPLES

(71) Applicant: Siemens Healthcare Diagnostics Inc., Tarrytown, NY (US)

(72) Inventors: Thomas Battersby, El Cerrito, CA (US); Adrian Nielsen Fehr, San Francisco, CA (US); Minxue Zheng, Foster City, CA (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 0 days.

(21) Appl. No.: 14/413,439

(22) PCT Filed: Jul. 18, 2013

(86) PCT No.: PCT/US2013/050999
§ 371 (c)(1),
(2) Date: Jan. 8, 2015

(87) PCT Pub. No.: WO2014/015098
PCT Pub. Date: Jan. 23, 2014

(65) Prior Publication Data
US 2015/0152407 A1    Jun. 4, 2015

Related U.S. Application Data

(60) Provisional application No. 61/672,833, filed on Jul. 18, 2012.

(51) Int. Cl.
C12N 15/10       (2006.01)
C12Q 1/68        (2006.01)

(52) U.S. Cl.
CPC ....... *C12N 15/1065* (2013.01); *C12Q 1/6806* (2013.01); *C12Q 1/6837* (2013.01); *C12Q 1/6874* (2013.01)

(58) Field of Classification Search
None
See application file for complete search history.

(56) References Cited

U.S. PATENT DOCUMENTS

| 2004/0253584 A1 | 12/2004 | Ihle et al. |
| 2006/0275782 A1 | 12/2006 | Gunderson et al. |
| 2011/0236997 A1 | 9/2011 | Battersby et al. |
| 2012/0142004 A1 | 6/2012 | Battersby et al. |

FOREIGN PATENT DOCUMENTS

| WO | 02061140 | 8/2002 |
| WO | 2006130347 | 12/2006 |
| WO | 2008121384 | 10/2008 |

OTHER PUBLICATIONS

International Search Report for PCT/US2013/050999 dated Feb. 12, 2013.

*Primary Examiner* — Kaijiang Zhang

(57) ABSTRACT

The present disclosure relates to normalization of biological samples, particularly samples comprising nucleic acids to be sequenced. The normalization protocols described herein may be utilized across multiple samples to cap total stoichiometric input and minimize variations in transcript abundance on a per-sample basis in a multiplexed fashion to dramatically increase the accuracy, capacity and efficiency of nucleic acid sequencing.

32 Claims, 4 Drawing Sheets

1. Library fragments terminated with unique capture tags

2. Capture moieties affixed to solid substrate at controlled stoichiometry

3. Library fragments (targets) hybridized to available capture oligos

4. Wash away unbound library fragments

5. Dissociate captured targets hyb-1 (Red)   hyb-N (Green)
hyb-2 (Blue)  Solid substrate (Light Blue)

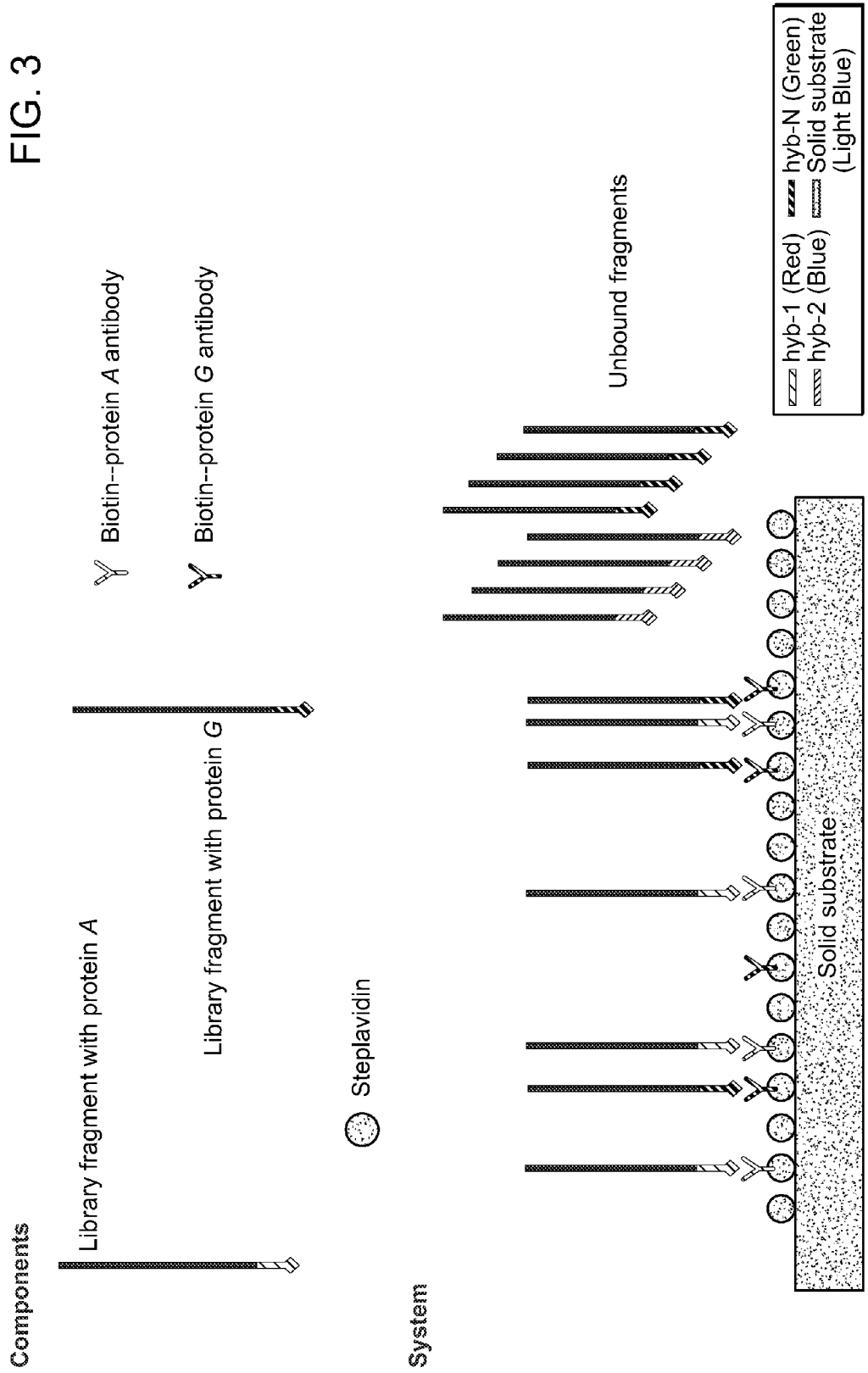

```
SEQUENCE LISTING

<160> NUMBER OF SEQ ID NOS: 10

<210> SEQ ID NO 1
<211> LENGTH: 35
<212> TYPE: DNA
<213> ORGANISM: Artificial Sequence
<220> FEATURE:
<223> OTHER INFORMATION: Artifificial Oligonucleotide

<400> SEQUENCE: 1 ttttttttttt ttcggcgaaa ctccgcaccg ccacg                             35

<210> SEQ ID NO 2
<211> LENGTH: 35
<212> TYPE: DNA
<213> ORGANISM: Artificial Sequence
<220> FEATURE:
<223> OTHER INFORMATION: Artificial Oligonucleotide

<400> SEQUENCE: 2 ttttttttttt tcccaggacg gcgctggcac gttga                             35

<210> SEQ ID NO 3
<211> LENGTH: 32
<212> TYPE: DNA
<213> ORGANISM: Artificial Sequence
<220> FEATURE:
<223> OTHER INFORMATION: Artificial Oligonucleotide

<400> SEQUENCE: 3 ttttttttcat gagcaagctg cagctgcgcg cg                                32

<210> SEQ ID NO 4
<211> LENGTH: 35
<212> TYPE: DNA
<213> ORGANISM: Artificial Sequence
<220> FEATURE:
<223> OTHER INFORMATION: Artificial Oligonucleotide

<400> SEQUENCE: 4 ttttttttttt aaagcgggcg gcgatcgcga atgtc                             35

<210> SEQ ID NO 5
<211> LENGTH: 35
<212> TYPE: DNA
<213> ORGANISM: Artificial Sequence
<220> FEATURE:
<223> OTHER INFORMATION: Artificial Oligonucleotide
```

```
<400> SEQUENCE: 5
tttttttttt gatggtgatc ccgcgcgtgc cgaaa                                35

<210> SEQ ID NO 6
<211> LENGTH: 35
<212> TYPE: DNA
<213> ORGANISM: Artificial Sequence
<220> FEATURE:
<223> OTHER INFORMATION: Artificial Oligonucleotide

<400> SEQUENCE: 6
tttttttttt tcgaattctc ggtgtccgcg ggcga                                35

<210> SEQ ID NO 7
<211> LENGTH: 35
<212> TYPE: DNA
<213> ORGANISM: Artificial Sequence
<220> FEATURE:
<223> OTHER INFORMATION: Artificial Oligonucleotide

<400> SEQUENCE: 7
tttttttttt atcttgcgcg gcagctcgtc gaccg                                35

<210> SEQ ID NO 8
<211> LENGTH: 35
<212> TYPE: DNA
<213> ORGANISM: Artificial Sequence
<220> FEATURE:
<223> OTHER INFORMATION: Artificial Oligonucleotide

<400> SEQUENCE: 8
tttttttttt ccggtcgatc gtggtgttcg cggct                                35

<210> SEQ ID NO 9
<211> LENGTH: 35
<212> TYPE: DNA
<213> ORGANISM: Artificial Sequence
<220> FEATURE:
<223> OTHER INFORMATION: Artificial Oligonucleotide

<400> SEQUENCE: 9
tttttttttt tgtgcgcccg agatcggtat cgccg                                35

<210> SEQ ID NO 10
<211> LENGTH: 35
<212> TYPE: DNA
<213> ORGANISM: Artificial Sequence
<220> FEATURE:
<223> OTHER INFORMATION: Artificial Oligonucleotide

<400> SEQUENCE: 10
tttttttttt cgacgcgggc ttggtacgtt tggcg                                35
```

METHOD OF NORMALIZING BIOLOGICAL SAMPLES

This application is the US National Stage of International Application No. PCT/US2013/050999, filed Jul. 18, 2013 and claims the benefit thereof. The International Application claims the benefit of U.S. Provisional Application No. 61/672,833 filed Jul. 18, 2012. Both of the applications are incorporated by reference herein in their entirety.

This application incorporates by reference the sequence listing which is submitted together with this application in computer readable form which has the file name 2012P10835US_SequenceListing.txt and is 3 KB.

BACKGROUND

Sequencing of nucleic acids, such as deoxyribonucleic acid (DNA) and ribonucleic acid (RNA), involves determining the order of the nucleotide bases, namely adenine, guanine, cytosine, uracil, and thymine contained within a genetic sample (e.g., DNA from a blood sample). Traditional Sanger sequencing generates a set of fragments with a common 5' origin and base-specific 3' termini. The 3' termini are created by base-specific interruption of in vitro enzymatic synthesis by the incorporation of chain-terminating nucleotide analogs. The fragments to be sequenced are typically cloned into a vector (e.g., bacteriophage M13) that allows the fragment to be isolated as single-stranded DNA, although similar methods can be applied for double-stranded DNA. However procured, isolated single-stranded DNA serves as a template for DNA polymerase-catalyzed reactions. The template is primed by an oligonucleotide primer complementary to a known or engineered sequence 3' to the sequence of interest. DNA polymerase extends the primer to copy the sequence of interest. The polymerase reactions take place in the presence of deoxyribonucleoside triphosphate analogs, 2',3'-dideoxyribonucleoside triphosphates (ddNTPs), which terminate chain extension because they lack 3' hydroxyl termini.

A series of fragments terminated in a particular base is generated by running the DNA polymerase reaction in the presence of equivalent concentrations of the four deoxyribonucleotide triphosphates (e.g., dCTP, dGTP, dTTP), plus a one-tenth concentration of one of the nucleotides in dideoxy form. Thus, the DNA polymerase will occasionally insert the dideoxy nucleotide adjacent to its complementary base in the target. This stops chain elongation, which results in the fragment being released from the polymerase. A series of double-stranded fragments of varying lengths is generated, with the newly synthesized strand of each fragment terminating in the selected dideoxynucleotide (e.g., ddATP), which identifies the complementary base (e.g., T) in the sequence of interest. Sites terminating in the other bases are identified by running comparable polymerase reactions with the other three dideoxy analogs. Traditionally, a radioactive label is included in the polymerization mixture. Thus, gel electrophoresis followed by radioautography can be used to generate four sequencing ladders, with each ladder specific to a particular base.

Variations of Sanger sequencing have been developed that allow for automated sequence determination. A red, blue, green or yellow fluorescent dye is attached to the 5' end of the sequencing primers. Each of the four sequencing reactions is run with a different color primer, thereby assigning characteristic fluorescence to all the fragments terminating in a particular base. Eliminating the use of radioisotopes favors high-throughput applications as the use of fluorescent dyes allows for automated determination of the sequence reads and processing of the data.

In modern automated Sanger sequencing systems, the sequence is determined by high-resolution electrophoretic separation of the end-labeled extension products in a capillary-based polymer gel. Laser excitation of the fluorescent labels as fragments of discrete lengths exit the capillaries, in combination with four-color detection of emission spectra, provide the sequencing trace. Software translates these traces into DNA sequence and generates error probabilities for each base-call. Applications of the Sanger system can now be applied to achieve read-lengths of approximately 1000 base pairs and accuracies above 99.9%.

Automated Sanger sequencing is referred to as a "first generation" technology. For all its accomplishments, Sanger sequencing is inherently limited by the polymerization and chemistry involved, which prompted development of systems more amenable to post-genomic (e.g., short-read), high-throughput sequencing. Newer, "next-generation sequencing" ("NGS") technologies can cheaply provide enormous volumes of sequence data (e.g., in excess of one billion short reads per sequencing runs). Thus, NGS technologies may be applied to a broad range of biological phenomena, including genetic variation, RNA expression, protein-DNA interactions, evolutionary comparisons, and chromosome conformation analyses. Current commercially available NGS technologies include Roche/454, Illumina/Solexa, Life/APG and Helicos Biosciences.

SUMMARY

The present disclosure relates to the preparation of biological samples to ensure high quality sequence reads in any sequencing method, including Sanger and NGS technologies. Specifically, the present invention discloses methods for normalizing inter- and intra-sample variability in the number of target sequences that are present in a given sample, set of samples, or library. For example, overabundant target sequences (e.g., greater than approximately 12 pM of total input library in the default 600 uL into the Illumina MiSeq sequencing system) can dramatically decrease the accuracy of sequence reads and overwhelm the ability to detect target sequences of lower abundance. In both conventional Sanger sequencing and NGS systems, signal strength is limited for low copy number target sequences. Embodiments of the present invention serve as metaphorical "buckets" to stoichiometrically limit or cap the amount of selected target or targets in any one reaction; in other words, once the "bucket" is full, no more targets are included and extreme variation among target numbers is minimized. Thus, high copy number sequences cannot overwhelm the sequence strength of low copy number transcripts. Moreover, the embodiments disclosed herein are applicable to multiplexed systems, which allows for selected targets from multiple samples to be predeterminitely tagged and pooled, thereby permitting for simultaneous analysis and consolidation of the number of downstream manipulations that need to applied in a given protocol. In preferred embodiments, normalization control is achieved in solution (i.e., the normalization control itself is not affixed to a solid support), which eliminates the need to quantitate and conjugate normalization controls to solid supports. Those of skill in the art will appreciate that the elegant insight disclosed herein is exceptionally customizable, allowing a user to select the type, number, origin and/or variation of targets while still in solution, and may be applied in a variety of experimental protocols, including, but not limited to, NGS systems.

Described herein is a method of normalizing biological samples, the method comprising: obtaining multiple samples, each sample comprising a plurality of targets; attaching capture tags to substantially all of the targets in a given sample, wherein each capture tag comprises an identifying feature and capture moiety-binding domain, both of which are unique to the sample to which it is added; pooling the samples; after or optionally before pooling, adding an amount of a capture moiety for each sample, wherein each capture moiety is specific for the capture moiety-binding domain of the capture tag utilized in a given sample, and wherein the total amount of each sample-specific capture moiety is equivalent across all samples, and is less than at least the most abundant target in any one of the samples; and capturing the targets.

In some embodiments, the targets comprise nucleic acid sequences. In some embodiments, the nucleic acid is DNA. In some embodiments, the targets comprise members of a DNA library. In some embodiments, the targets are fragmented prior to attaching the capture tags.

In some embodiments, wherein the capture tags are oligonucleotides. In some embodiments, the capture tags are deoxyribonucleotides. In some embodiments, the capture tags are ligated to the target. In some embodiments, the capture tags are incorporated into the target through PCR amplification. In some embodiments, the capture tags are at least partially single-stranded. In some embodiments, the identifying feature is a specified DNA sequence within the capture tag. In some embodiments, the capture tags are approximately 35 base pairs. In some embodiments, the capture tags further comprise base modifications.

In some embodiments, the capture moieties are oligonucleotides. In some embodiments, the capture moiety oligonucleotides comprise a sequence complementary to oligonucleotide capture tags attached to the targets. In some embodiments, both the capture moiety oligonucleotides and the capture tag oligonucleotides are DNA.

In some embodiments, capturing the targets comprises affixing the capture moieties to a solid support. In some embodiments, the solid support is a selected from a group consisting of magnetic beads, non-magnetic beads, capillary tubes, closed flow cells and open wells. In certain embodiments, wherein the solid support is a paramagnetic micron bead. In some embodiments, the solid supports are 100 nm by 1 um by 1 um in dimension.

In some embodiments, the capture moieties are covalently attached to the solid support. In some embodiments, the capture moieties are covalent attached through amine coupling or azide-alkyne cycloaddition.

In some embodiments, the capture moieties comprise a first part that binds to the capture tags and a second part that binds to universal oligonucleotide probes attached to the solid support. In some embodiments, the probes are oligonucleotides. In some embodiments, each oligonucleotide probe comprises an identical nucleotide sequence capable of hybridizing to a corresponding sequence found in each capture moiety. In certain embodiments, the oligonucleotides are DNA. In some embodiments, wherein the parts are terminal. In some embodiments, the ratio of capture moieties to probes is approximately 1:2 to 1:100.

In some embodiments, the probes are streptavidin, the capture moieties are biotinylated antibodies, and the capture tags attached to the targets are proteins bound by the antibodies. In some embodiments, the antibodies are monoclonal.

In some embodiments of the invention, the methods further comprise removing the capture tag from the target by exposure to non-hybridizing conditions, photocleavage, chemical cleavage, or restriction endonucleases.

In some embodiments of the invention, the methods further comprise detaching the targets from the capture moieties. In some embodiments of the invention, detachment is effected by altering hybridization conditions.

In some embodiments of the invention, the methods further comprise sequencing the captured targets. In some embodiments, the targets are polynucleotides. In some embodiments, the targets are clonally amplified before or immediately after attachment of the capture tags. In some embodiments, the targets are sequenced as single-molecule templates. In some embodiments, sequencing is done by a sequencing platform selected from the group comprising Roche 454 platform, Illumina Genomic Analyzer, SOLID system, or Helicos True Single Molecule DNA sequencing.

In some embodiments of the invention, the steps of the methods are performed sequentially. In some embodiments, the steps are performed iteratively.

Further disclosed herein is a kit comprising a plurality of oligonucleotide capture tags capable of binding target polynucleotides, wherein each capture tag comprises a unique identifying and is at least partially single stranded; an oligonucleotide capture moiety capable of binding the capture tag in solution, wherein each capture moiety comprises a first part that binds to the capture tags and a second part that binds to probes attached to the solid support; and a solid support comprising universal oligonucleotide probes capable of binding the capture moiety, wherein the probes comprise an identical nucleotide sequence capable of hybridizing to a corresponding sequence found in each capture moiety.

BRIEF DESCRIPTION OF THE DRAWING

FIG. 3 presents an embodiment in which the universal binding probe is streptavidin, the capture probe is biotinylated antibody specific to protein A or G, and the library fragments are terminated in proteins recognized by the biotinylated antibody.

DEFINITIONS

Figure 1:
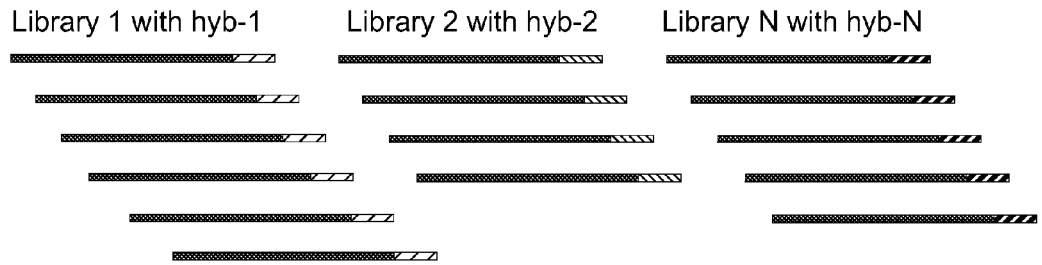
FIG. 1 presents an overview of an embodiment of the invention in which each set of library fragments (e.g., one per sample or per patient) is terminated with a unique single-stranded capture tag (hyb-1, hyb-2, hyb-N), capable of binding to a complementary capture moiety (in this example, oligonucleotides) affixed to a solid support. In this particular embodiment, the stoichiometry of the capture moieties is controlled via the solid support.
Figure 1:
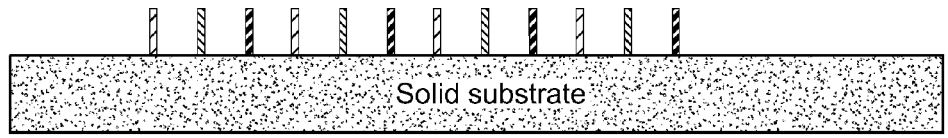
Figure 1:
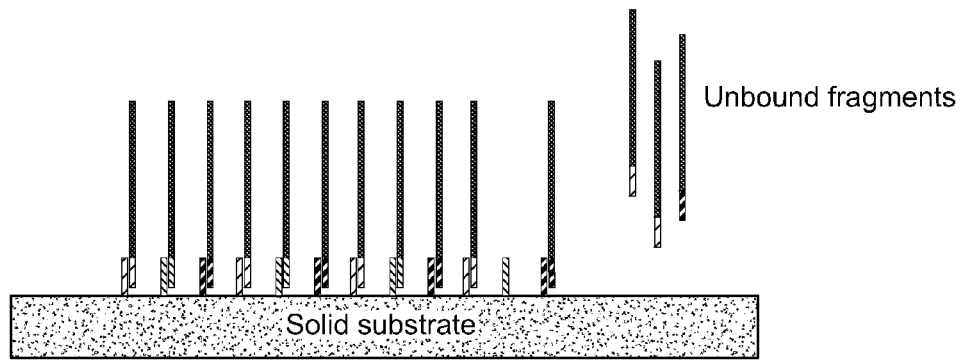
Figure 1:
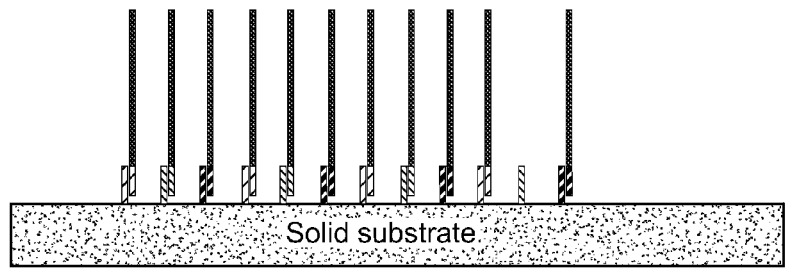

The term "amplification" or "amplification reaction" is used herein to refer to any in vitro process for exponentially increasing the number of copies of a nucleotide sequence or sequences. Nucleic acid amplification results in the incorporation of nucleotides (ribonucleotides or deoxyribonucleotides) into primers to form DNA or RNA molecules that are complementary to a template nucleic acid molecule. As used herein, one amplification reaction may consist of many rounds of primer extension. For example, one PCR reaction may consist of several cycles of denaturation and extension ranging from, e.g., about 5 cycles to about 1000 cycles, or more.

The term "amplification reaction reagents", is used herein to refer to reagents used in nucleic acid amplification reactions and may include, but are not limited to, buffers, enzymes having reverse transcriptase and/or polymerase activity or exonuclease activity, enzyme cofactors such as magnesium or manganese, salts, nicotinamide adenine dinuclease (NAD) and deoxynucleoside triphosphates (dNTPs), such as deoxyadenosine triphosphate, deoxyguanosine triphosphate, deoxycytidine triphosphate and deoxythymidine triphosphate.

The term "capture moiety" is used herein to refer to an entity capable of binding to a tag attached to a target when brought into contact with the target or tag. In embodiments of the invention disclosed herein, target normalization is effected by controlling the amount and type (i.e., target specificity or identifying feature) of capture moiety used to capture a target of interest. For example, samples may be obtained from a plurality of subjects and all, or a selected group, of targets within a given sample are attached to a tag with a motif that is specific for a particular capture moiety and unique to that sample. If the samples are pooled, control of the capture moieties allows a user to select only targets that correspond to the capture moiety of choice. By including only specific quantities of the capture moiety of choice (e.g., a quantity within an optimized input range for a given sequencing platform), any target in excess of those quantities will not be bound and can be eliminated from downstream processing (e.g., sequencing). Inclusion of a unique identifying feature within the tags or the capture moieties allows the targets to be distinguished and correlated with their original sample after pooling. For example, in some embodiments, a capture moiety comprises a polynucleotide sequence and the corresponding tag comprises a sequence complementary to that sequence, such that the capture tag is capable of specifically hybridizing with the capture moiety. Capture moieties may be DNA or RNA, single- or double-stranded, or any combination thereof. In some embodiments, the capture moieties are affixed directly to a solid support. In other, preferred embodiments, capture moieties bind (e.g., hybridize) to tags in solution. In such embodiments, the capture moieties are subsequently and indirectly captured on a solid support via a universal probe capable of binding all the capture moieties in a given sample or pooled set of samples irrespective of the target to which the capture moiety is bound. Thus, selection of the type and amount of capture moieties may be used as normalization controls in solution to select particular species of targets and cap the amount of the targets as necessary for downstream processing.

The term "equivalent", as used herein, refers to a quantity of capture moiety or moieties applied to pooled samples as necessary to affect the amount of at least one target in at least one of the samples (i.e., to capture less than all of the copies of a particular target from at least one of the samples), such that the amount of the target has the same significance across all of the samples. Depending on the amount of target present from each sample, an "equivalent" amount can be identical across all samples, or differ by a factor of at least 2×, 3×, 4×, 5×, 6×, etc. for at least one of the samples. In some embodiments, equivalence is achieved by adding capture moiety at specific ratios between certain samples (in the range 1:2, 1:10, 1:100, 1:1,000 to 1:1,000,000).

The term "gene", as used herein, has its art understood meaning, and refers to a part of the genome specifying a macromolecular product, be it DNA for incorporation into a host genome, a functional RNA molecule or a protein, and may include regulatory sequences (e.g., promoters, enhancers, etc.) and/or intron sequences preceding (5' non-coding sequences) and following (3' non-coding sequences) the coding sequences.

The term "hybridization", as used herein, refers to the formation of complexes (also called duplexes or hybrids) between nucleotide sequences which are sufficiently complementary to form complexes via Watson-Crick base pairing or non-canonical base pairing. It will be appreciated that hybridizing sequences need not have perfect complementary to provide stable hybrids. In many situations, stable hybrids will form where fewer than about 10% of the bases are mismatches. Accordingly, as used herein, the term "complementary" refers to a nucleic acid molecule that forms a stable duplex with its complement under particular conditions, generally where there is about 90% or greater homology (e.g., about 95% or greater, about 98% or greater, or about 99% or greater homology). Those skilled in the art understand how to estimate and adjust the stringency of hybridization conditions such that sequences that have at least a desired level of complementarity will stably hybridize, while those having lower complementarity will not. For examples of hybridization conditions and parameters, see, for example, Sambrook et al., "*Molecular Cloning: A Laboratory Manual*", 1989, Second Edition, Cold Spring Harbor Press: Plainview, N.Y. and Ausubel, "*Current Protocols in Molecular Biology*", 1994, John Wiley & Sons: Secaucus, N.J. Complementarity between two nucleic acid molecules is said to be "complete", "total" or "perfect" if all the nucleic acid's bases are matched, and is said to be "partial" otherwise.

The terms "labeled" and "labeled with a detectable agent (or moiety)" are used herein interchangeably to specify that an entity (e.g., a target sequence) can be visualized, e.g., directly or following hybridization to another entity that comprises a detectable agent or moiety. Preferably, the detectable agent or moiety is selected such that it generates a signal which can be measured and whose intensity is related to (e.g., proportional to) the amount of the entity of interest (e.g., a target sequence). Methods for labeling nucleic acid molecules are well-known in the art. In some embodiments, labeled nucleic acids can be prepared by incorporation of, or conjugation to, a label that is directly or indirectly detectable by spectroscopic, photochemical, biochemical, immunochemical, electrical, optical, or chemical means.

The term "library" is used herein in its broadest sense and refers to any collection of a plurality of targets. In some embodiments, a library comprises all the targets in a given sample. In some embodiments, a library is representative of all the targets in a given sample (e.g., an equivalent cross-sampling). Libraries may be comprised of natural or synthetic DNA, RNA, mRNA, genes, polynucleotides, etc.

The term "melting temperature" or "Tm" of a specific oligonucleotide, as used herein, refers to the specific temperature at which half of the oligonucleotide hybridizes to its target in equilibrium. Accurate prediction of the Tm of any oligonucleotide can be made based on sequence using nearest neighbor parameter calculations.

The term "nucleoside" as used herein, refers to adenine ("A"), guanine ("G"), cytosine ("C"), uracil ("U"), thymine ("T") and analogs thereof linked to a carbohydrate, for example D-ribose (in RNA) or 2'-deoxy-D-ribose (in DNA), through an N-glycosidic bond between the anomeric carbon of the carbohydrate (1'-carbon atom of the carbohydrate) and the nucleobase. When the nucleobase is purine, e.g., A or G, the ribose sugar is generally attached to the N9-position of the heterocyclic ring of the purine. When the nucleobase is pyrimidine, e.g., C, T or U, the sugar is generally attached to the N1-position of the heterocyclic ring. The carbohydrate may be substituted or unsubstituted. Substituted ribose sugars include, but are not limited to, those in which one or more of the carbon atoms, for example the 2'-carbon atom, is substituted with one or more of the same or different Cl, F, —R, —OR, —NR$_2$ or halogen groups, where each R is independently H, $C_1$-$C_6$ alkyl or $C_5$-$C_{14}$ aryl. Ribose examples include ribose, 2'-deoxyribose, 2',3'-dideoxyribose, 2'-haloribose, 2'-fluororibose, 2'-chlororibose, and 2'-alkylribose, e.g., 2'-O-methyl, 4'-alpha-anomeric nucleotides, 1'-alpha-anomeric nucleotides (Asseline et al., Nucl. Acids Res., 19:4067-74 [1991]), 2'-4'- and 3'-4'-linked and other "locked" or "LNA," bicyclic sugar modifications (WO 98/22489; WO 98/39502; WO 99/14226).

The term "nucleotide" as used herein means a nucleoside in a phosphorylated form (a phosphate ester of a nucleoside), as a monomer unit or within a polynucleotide polymer. "Nucleotide 5'-triphosphate" refers to a nucleotide with a triphosphate ester group at the 5' position, sometimes denoted as "NTP", or "dNTP" and "ddNTP" to particularly point out the structural features of the ribose sugar. The triphosphate ester group may include sulfur substitutions for the various oxygen moieties, e.g., alpha-thio-nucleotide 5'-triphosphates. Nucleotides can exist in the mono-, di-, or tri-phosphorylated forms. The carbon atoms of the ribose present in nucleotides are designated with a prime character (') to distinguish them from the backbone numbering in the bases. For a review of polynucleotide and nucleic acid chemistry see Shabarova, Z. and Bogdanov, A. Advanced Organic Chemistry of Nucleic Acids, VCH, New York, 1994.

The terms "nucleic acid", "nucleic acid molecule", "polynucleotide" or "oligonucleotide" are used herein interchangeably. They refer to polymers of nucleotide monomers or analogs thereof, such as deoxyribonucleic acid (DNA) and ribonucleic acid (RNA). The nucleotides may be genomic, synthetic or semi-synthetic in origin. Unless otherwise stated, the terms encompass nucleic acid-like structures with synthetic backbones, as well as amplification products. As will be appreciated by one skilled in the art, the length of these polymers (i.e., the number of nucleotides it contains) can vary widely, often depending on their intended function or use. Polynucleotides can be linear, branched linear, or circular molecules. Polynucleotides also have associated counter ions, such as H$^+$, NH$_4^+$, trialkylammonium, Mg$_2^+$, Na$^+$ and the like. A polynucleotide may be composed entirely of deoxyribonucleotides, entirely of ribonucleotides, or chimeric mixtures thereof. Polynucleotides may be composed of internucleotide nucleobase and sugar analogs.

In some embodiments, the term "oligonucleotide" is used herein to denote a polynucleotide that comprises between about 5 and about 150 nucleotides, e.g., between about 10 and about 100 nucleotides, between about 15 and about 75 nucleotides, or between about 15 and about 50 nucleotides. Throughout the specification, whenever an oligonucleotide is represented by a sequence of letters (chosen, for example, from the four base letters: A, C, G, and T, which denote adenosine, cytidine, guanosine, and thymidine, respectively), the nucleotides are presented in the 5' to 3' order from the left to the right. A "polynucleotide sequence" refers to the sequence of nucleotide monomers along the polymer. Unless denoted otherwise, whenever a polynucleotide sequence is represented, it will be understood that the nucleotides are in 5' to 3' orientation from left to right. The term "nucleic acid" as used herein means a nucleobase polymer having a backbone of alternating sugar and phosphate units in DNA and RNA. "Nucleic acid" and "polynucleotide" are considered to be equivalent and interchangeable. Nucleic acids are commonly in the form of DNA or RNA.

Nucleic acids, polynucleotides and oligonucleotides may be comprised of standard nucleotide bases or substituted with nucleotide isoform analogs, including, but not limited to iso-C and iso-G bases, which may hybridize more or less permissibly than standard bases, and which will preferentially hybridize with complementary isoform analog bases. Many such isoform bases are described, for example, by Benner et al., (1987) Cold Spring Harb. Symp. Quant. Biol. 52, 53-63. Analogs of naturally occurring nucleotide monomers include, for example, 7-deazaadenine, 7-deazaguanine, 7-deaza-8-azaguanine, 7-deaza-8-azaadenine, inosine, nebularine, nitropyrrole (Bergstrom, J. Amer. Chem. Soc., 117: 1201-1209 [1995]), nitroindole, 2-aminopurine, 2-amino-6-chloropurine, 2,6-diaminopurine, hypoxanthine, pseudouridine, pseudocytosine, pseudoisocytosine, 5-propynylcytosine, isocytosine, isoguanine (Seela, U.S. Pat. No. 6,147,199), 7-deazaguanine (Seela, U.S. Pat. No. 5,990, 303), 2-azapurine (Seela, WO 01/16149), 2-thiopyrimidine, 6-thioguanine, 4-thiothymine, 4-thiouracil, 0-6-methylguanine, N-6-methyladenine, O-4-methylthymine, 5,6-dihydrothymine, 5,6-dihydrouracil, 4-methylindole, pyrazolo[3,4-D]pyrimidines, "PPG" (Meyer, U.S. Pat. Nos. 6,143,877 and 6,127,121; Gall, WO 01/38584), and ethenoadenine (Fasman (1989) in Practical Handbook of Biochemistry and Molecular Biology, pp. 385-394, CRC Press, Boca Raton, Fla.).

The term "3'" refers to a region or position in a polynucleotide or oligonucleotide 3' (i.e., downstream) from another region or position in the same polynucleotide or oligonucleotide. The term "5'" refers to a region or position in a polynucleotide or oligonucleotide 5' (i.e., upstream) from another region or position in the same polynucleotide or oligonucleotide. The terms "3' end" and "3' terminus", as used herein in reference to a nucleic acid molecule, refer to the end of the nucleic acid which contains a free hydroxyl group attached to the 3' carbon of the terminal pentose sugar. In some embodiments of the invention, targets are tagged at their 3' terminus. The term "5' end" and "5' terminus", as used herein in reference to a nucleic acid molecule, refers to the end of the nucleic acid molecule which contains a free hydroxyl or phosphate group attached to the 5' carbon of the terminal pentose sugar. In some embodiments of the invention, targets are tagged at their 5' terminus.

The term "isolated", as used herein, means a target, sample, polynucleotide, nucleic acid or oligonucleotide, which by virtue of its origin or manipulation, is separated from at least some of the components with which it is naturally associated or with which it is associated when initially obtained. By "isolated", it is alternatively or additionally meant that the target, sample, polynucleotide, nucleic acid or oligonucleotide of interest is produced or synthesized by the hand of man.

The terms "normalization" or "normalized" as used herein refer to a minimization of numerical variation between and/or within a sample or samples. Stated another way, any biological sample may have multiple distinct targets (e.g., mRNAs) and multiple copies of each distinct target (e.g., transcript or copy number). The number of copies for each is independent of the number of copies of every other target. Thus, in the sample as a whole, there exists a spectrum of total copy numbers of all targets, which may range, for example, from 1 to $10^{10}$. As used herein, normalization refers to a reduction in the numbers of those targets with copy numbers towards the high-end of the spectrum. The number of these targets is capped in a pre-determined or selected manner to control the number of those targets post-normalization. This normalization occurs independently of non-targets or contaminants. In some embodiments, normalization occurs within a single sample. In some embodiments normalization occurs between samples such that the numerical range of targets is approximately equivalent across all samples, i.e., so that the high copy number targets are equivalently capped across all samples.

The term "primer", as used herein, typically refers to oligonucleotides that hybridize in a sequence specific manner to a complementary nucleic acid molecule (e.g., a nucleic acid molecule comprising a target sequence). In some embodiments, a primer will comprise a region of nucleotide sequence that hybridizes to at least about 8, e.g., at least about 10, at least about 15, or about 20 to about 40 consecutive nucleotides of a target nucleic acid (i.e., will hybridize to a contiguous sequence of the target nucleic acid). In general, a primer sequence is identified as being either "complementary" (i.e., complementary to the coding or sense strand (+)), or "reverse complementary" (i.e., complementary to the anti-sense strand (−)). In some embodiments, the term "primer" may refer to an oligonucleotide that acts as a point of initiation of a template-directed synthesis using methods such as PCR (polymerase chain reaction) or LCR (ligase chain reaction) under appropriate conditions (e.g., in the presence of four different nucleotide triphosphates and a polymerization agent, such as DNA polymerase, RNA polymerase or reverse-transcriptase, DNA ligase, etc., in an appropriate buffer solution containing any necessary reagents and at suitable temperature(s)). Such a template directed synthesis is also called "primer extension". For example, a primer pair may be designed to amplify a region of DNA using PCR. Such a pair will include a "forward primer" and a "reverse primer" that hybridize to complementary strands of a DNA molecule and that delimit a region to be synthesized and/or amplified.

As used herein, the term "sample" refers to a biological sample obtained or derived from a source of interest, as described herein. In some embodiments, a source of interest comprises an organism, such as an animal or human. In some embodiments, a sample comprises nucleic acids or a set of nucleic acids (e.g., library) representing all or substantially of the nucleic acid sequences found in a source. In some embodiments, a biological sample or source of the sample comprises biological tissue or fluid. In some embodiments, a biological sample or source of the sample may be or comprise bone marrow, blood, blood cells, ascites, tissue or fine needle biopsy samples, cell-containing body fluids, free floating nucleic acids, sputum, saliva, urine, cerebrospinal fluid, peritoneal fluid, pleural fluid, feces, lymph, gynecological fluids, skin swabs, vaginal swabs, oral swabs, nasal swabs, washings or lavages such as a ductal lavages or broncheoalveolar lavages, aspirates, scrapings, bone marrow specimens, tissue biopsy specimens, surgical specimens, feces, other body fluids, secretions, and/or excretions, and/or cells therefrom, etc. In some embodiments, a biological sample or source of the sample is or comprises cells obtained from an individual. In some embodiments, obtained cells are or include cells from an individual from whom the sample is obtained. In some embodiments, obtained cells are or include microbial cells of an individual's microbiome. In some embodiments, a sample or source is a "primary sample" if it is obtained directly from a source of interest by any appropriate means. For example, in some embodiments, a primary biological sample is obtained by methods selected from the group consisting of biopsy (e.g., fine needle aspiration or tissue biopsy), surgery, collection of body fluid (e.g., blood, lymph, feces, etc.), etc. In some embodiments, as will be clear from context, the term "sample" refers to a preparation that is obtained by processing (e.g., by removing one or more components of and/or by adding one or more agents to) a primary sample or source. For example, filtering using a semi-permeable membrane. For example, a "secondary sample" or "processed sample" may comprise nucleic acids or proteins extracted from a "primary sample" or obtained by subjecting a "primary sample" to techniques such as amplification or reverse transcription of mRNA, isolation and/or purification of certain components, etc.

As used herein, the terms "sequence determination", "determining a nucleotide sequence", "sequencing", and like terms, in reference to polynucleotides includes determination of partial as well as full sequence information of the polynucleotide. That is, the term includes sequence comparisons, fingerprinting, and like levels of information about a target polynucleotide, as well as the express identification and ordering of each nucleoside of the target polynucleotide within a region of interest. In various embodiments "sequence determination" comprises identifying a single nucleotide, while in various embodiments more than one nucleotide is identified. Identification of nucleosides, nucleotides, and/or bases are considered equivalent herein. It is noted that performing sequence determination on a polynucleotide typically yields equivalent information regarding the sequence of a perfectly complementary (100% complementary) polynucleotide and thus is equivalent to sequence determination performed directly on a perfectly complementary polynucleotide.

The methods disclosed herein are not limited to or by particular sequencing platforms. Nonetheless, exemplary sequencing reactions include those based on techniques developed by Maxam and Gilbert, *Proc. Natl. Acad Sci USA,* 74:560, 1977 or Sanger, *Proc. Nat. Acad. Sci* 74:5463, 1977. It is also contemplated that any of a variety of automated sequencing procedures may be utilized when performing subject assays (*Biotechniques* 19:448, 1995, Venter et al., *Science,* 291:1304-1351, 2001, Lander et al., *Nature,* 409: 860-921, 2001), including sequencing by mass spectrometry (see, for example, U.S. Pat. No. 5,547,835 and international patent application Publication Number WO 94/16101, entitled DNA Sequencing by Mass Spectrometry by H. Koster, U.S. Pat. No. 5,547,835 and international patent application Publication Number WO 94/21822 entitled "DNA Sequencing by Mass Spectrometry Via Exonuclease Degradation" by H. Koster), and U.S. Pat. No. 5,605,798 and International Patent Application No. PCT/US96/03651 entitled DNA Diagnostics Based on Mass Spectrometry by H. Koster, Cohen et al. (1996) *Adv. Chromatogr.* 36:127- 162, and Griffin et al. (1993) *Appl. Biochem. Biotechnol.* 38:147-159). It will be evident to one skilled in the art that, for certain embodiments, occurrence of only one, two or three nucleic acid bases need be determined in a sequencing reaction. Yet other sequencing methods are disclosed, e.g., in U.S. Pat. No. 5,580,732 entitled "Method of DNA sequencing employing a mixed DNA-polymer chain probe" and U.S. Pat. No. 5,571,676 entitled "Method for mismatch-directed in vitro DNA sequencing", and in Melamede, U.S. Pat. No. 4,863,849, Cheeseman, U.S. Pat. No. 5,302,509, Tsien et al, International application WO 91/06678, Rosenthal et al, International application WO 93/21340, Canard et al, Gene, 148: 1-6 (1994), Metzker et al, *Nucleic Acids Research*, 22: 4259-4267 (1994) and U.S. Pat. Nos. 5,740,341 and 6,306,597. Exemplary NGS techniques for use in embodiments of the invention include those described in Metzker, M. L., *Nature Review Genetics*, 2010, 11:31-46, and Shendure J. and Hanlee, J., *Nat. Biotech.*, 2008, 26:1135-1145.

The term "tag", as used herein, refers to any molecule capable of being attached to a target of interest. For example, in some embodiments of the invention, sequences of DNA or RNA are appended to a target-of-interest. In some embodiments of the invention, a sample is obtained and targets within the sample are tagged. In some embodiments, multiple samples are obtained, pooled, and targets within the sample are then tagged, and the tagged targets in the sample are combined or pooled with differentially tagged targets from other samples. In some embodiments, the tags are at least partially single-stranded. In some embodiments, the appended sequences are identical for all targets in a particular sample and unique to the sample being assessed. The presence of such a unique identifying feature or "barcode" allows the identification of the source of each tagged target within a pooled library, which drastically improves sequencing capacity. In some embodiments, the appended sequences are unique to a particular target or group of targets in a particular sample (i.e., inter-sample differential tagging) and are identical across multiple samples. In some embodiments, the appended sequences are identical for all targets in a particular sample and unique for each sample in a plurality of samples. In some embodiments, tags may comprise proteins or polypeptides capable of binding to or interacting with another polypeptide such as an antibody. In some embodiments tags, comprise at least two domains: a first domain comprising an identifying feature unique to the sample or target to which it is added/attached; and a second binding domain capable of binding to a capture moiety. In some embodiments, the identifying feature is a nucleotide sequence, and the binding domain is a nucleotide sequence comprising a hybridization domain. In some embodiments, the identifying feature unique to the sample or target and the hybridization domain may comprise the same nucleotide sequence (i.e., a single nucleotide sequence that can serve as both a unique identifier and that can stably hybridize with a corresponding sequence under reasonable reaction conditions). The unique identifying feature may alternatively be referred to as "zip codes" or "barcodes". Inter-sample or intra-sample differentially tagged targets may be mixed, amplified and distinguished using the unique identifying features found within the tags appended to the targets prior to processing. Thus, embodiments of the invention allow one to sequence a variety of nucleic acid targets across a variety of samples at the same time. In other words, the presence of an identifying feature or barcode allows the identification of the source of each tagged target within a pooled library. Those of skill in the art will also appreciate that the unique identifying feature can be incorporated, in whole or in part, into the capture moieties described above.

The term "target" is used herein to refer to any specimen-, nucleic acid- or polynucleotide-of-interest in a sample (e.g., DNA library nucleotide fragment) that is desired or selected to be normalized through the methods disclosed herein. In some embodiments, a target may be a nucleic acid. The target may be a gene, a regulatory sequence, genomic DNA, environmental DNA, cDNA, mRNA or any portion of the foregoing. In other embodiments, a target may be a protein. In one example, a target may comprise a particular cDNA in a cDNA library derived from a particular cell type in a subject. Multiple targets may be present in a sample and multiple copies of the same target may exist in a sample. In some embodiments, a target is any molecule (e.g., polynucleotide) to which a capture tag is attached. The choice of targets in the methods disclosed herein and the stoichiometric cap applied to any one target or group of targets is limited only by the discretion of an individual user.

In some embodiments of the invention, at least a portion of both the target and the tag will be single-stranded. In other embodiments, however, only one or the other is single-stranded. Furthermore, in some embodiments of the invention, one or other of the target or tag is double-stranded polynucleotides.

DETAILED DESCRIPTION OF SOME EMBODIMENTS

Next generation sequencing (NGS), as used herein, refers to array-based sequencing protocols utilizing cycles of enzymatic manipulation and imaging-based data collection. Widely used NGS platforms include 454 sequencing, Illumina/Solexa technology, the SOLiD platform, the Polonator, and the HeliScope Single Molecule Sequencer Technology. In most platforms, genomic or other target DNA is randomly fragmented and ligated in vitro to common adaptor sequences to form templates that are attached or immobilized (directly or indirectly) to a solid support. Immobilization of spatially separated template sites allows thousands to billions of sequencing reactions to be performed simultaneously. In certain NGS platforms, templates are clonally amplified by emulsion PCR, bridge PCR (see, e.g., Adessi et al., *Nucleic Acids Res.*, 2000, 28:e87; Fedurco et al., *Nucleic Acids Res.*, 2006, 34:e22) or in situ polonyzation (Mitra and Church, *Nucleic Acids Res.*, 1999, 27:e34). Other NGS platforms (e.g., HeliScope) utilize single-molecule templates, i.e., a single molecule is spatially separated and immobilized (e.g., bound by a primer attached to solid support) on a solid support and subject to enzymatic manipulation without the need for amplification. NGS platforms also differ in the type of enzymatic manipulation that is applied. Several widely used platforms rely on "sequencing-by-synthesis", in which a DNA polymerase serially extends a primed and bound template by incorporation of fluorescently labeled nucleotides. Enzymatic manipulation in some platforms is achieved via a ligase, in which a fluorescently labeled probe hybridizes to its complementary sequence adjacent a primed template and DNA ligase is added to join the dye-labeled probe to the primer.

NGS platforms are essential to a wide range of molecular biology applications including de novo genome sequencing, re-sequencing, detection and profiling of coding and non-coding transcripts (e.g., cap analysis of gene expression, serial analysis of gene expression), identification of sequence variants, epigenetic profiling, and interaction mapping. NGS platforms for use in embodiments of the invention have been described previously. See, for example, Metzker, M. L., *Nature Review Genetics*, 2010, 11:31-46;

Shendure J. and Hanlee, J., *Nat. Biotech.*, 2008, 26:1135-1145. Compared with microarrays, previously used for many of these applications, NGS offers a higher dynamic range, enabling the detection of rare transcripts and splice variants in the transcriptome as well as rare genomic polymorphism, e.g., somatic mutations present within cancer samples. It remains a challenge, however, to distinguish sequence variation from sequencing errors.

Many errors in NGS sequencing are platform-dependent, i.e., each of the major commercial systems introduces its own biases into the sequence data, e.g., see Minoche, et al. "Evaluation of genomic high-throughput sequencing data generated on Illumina HiSeq and Genome Analyzer systems", *Genome Biology*, 2011, 12:R112. A non-random distribution of the reads in the sequenced sample (e.g., preferences of certain base substitution errors and sequence context; wrong base calls) have profound implications on the interpretation of results. For example, a non-random read distribution can bias profiling of transcripts and hamper the detection of sequence polymorphisms in regions of low sequence coverage. Errors in the reads can result in false positive variant calls or wrong consensus sequences.

Embodiments of present invention result from the realization that a significant source of error in NGS sequencing is platform-independent. The sequencing of multiple targets in biological samples, particularly across multiple samples, is hampered by the presence of overly abundant targets, i.e., those targets present at high copy number. If sequencing the members of a DNA library, for example, there need only be a sufficient number of copies of each member to ensure that each position in the molecule can be associated with a nucleotide. NGS systems require that the number of input nucleic acid library fragments (DNA or RNA, possibly with non-natural or modified bases) be within a narrow range. This range ensures that sufficient coverage per reference position is ultimately obtained (thereby giving confidence to the consensus sequence), but not so high that output sequencing signals from spatially proximal fragments interfere and degrade read quality (e.g., in the case of light from geographically-localized clusters on a flow-cell for Illumina's sequencing-by-synthesis technology, loading multiple active template/enzyme complexes into an individual Pacific Biosciences' zero mode waveguide, or oil droplet microreactors in Ion Torrent's emulsion PCR where single nucleic acid fragments are needed per droplet).

Another attribute of NGS techniques is that numerous unique samples (e.g., from various patients) are often pooled together and run simultaneously, with subsequent sorting based on unique DNA "barcodes" per sample, i.e., multiplexing. Multiplex DNA sequencing is well known in the art (see, e.g., Church, G. M. and Kieffer-Higgins, S., "Multiplex DNA Sequencing", *Science*, 1988, 240:185-188). However, accurately and efficiently normalizing the input libraries per sample remains an unsolved problem with various slow and partial solutions currently in use. As a non-limiting example of the importance of this problem, if a single patient sample (or several) has an unusually high input nucleic acid fragment concentration, this single sample (unless normalized) could easily push the overall nucleic acid fragment quantity for that sequencing run above the operational limits such that all samples, including the "high" sample, have diminished sequencing quality.

Thus, embodiments of present invention normalize sequencing samples to decrease high copy number target variation and multiplexing NGS sequencing errors. Embodiments of the invention are applicable to pools of samples (for example, library pools), as the methods disclosed herein prevent individual high concentration samples from excluding data collection for low concentration samples, without the requirement of quantitating libraries individually. Capping the maximal representation per sample (or library) in a targeted and multiplexed manner, and within an accepted range (for example, less than approximately 12 pM of total input library in the default 600 uL into the Illumina MiSeq sequencing system) for NGS instruments, dramatically improves sequencing efficiency and accuracy.

Targets

Applicable targets in embodiments of the invention can be derived from virtually any source. Typically, the targets will be nucleic acid molecules, although they may also comprise polypeptides. Targets may be derived from representative locations along a chromosome of interest, a chromosomal region of interest, an entire genome of interest, a cDNA library, RNA library and the like. Target nucleic acids may be relatively long (typically thousands of bases) random or non-random fragments of nucleic acid obtained by methods well-known to those of skill in the art, as described below.

Targets may be obtained from samples. Samples can be obtained from a single source (e.g., one patient or tissue) or from multiple sources. Samples may be obtained from a plurality of subjects, tissues, etc. In some embodiments, samples are obtained from a single subject at multiple time points and the differences between the time points ascertained.

In some embodiments of the invention, targets are capped on a per target basis. That is, the absolute number (e.g., copy number) of a target or set of targets is controlled to be less than a specified amount. For example, in some embodiments of the invention, the level of a particular target is capped to be less than 1000, 900, 800, 700, 600, 500, 400, 300, 200, 100, 90, 80, 70, 60, 50, 40, 30, 20, 10, 5 or fewer copies. In some embodiments of the invention, targets are capped by amount. For example, the amount of a particular target may be capped to be less than 10 μg, 5 μg, 1 μg, 500 ηg, 100 ηg, 90 ηg, 80 ηg, 70 ηg, 60 ηg, 50 ηg, 40 ηg, 30 ηg, 20 ηg, 10 ηg, 5 ηg, 1 ηg, 500 picograms, etc. The target cap appropriate for a given application may be influenced by a variety of factors, including sample type, sample number, sample amount, or sequencing platform. Those of skill in the art will appreciate that the cap may be set as necessary for any given post-normalization application.

Preparation of RNA

In some embodiments, the disclosed methods may involve some level of RNA preparation. The targets described above may themselves be RNA, or the targets may be a fragmented cDNA library produced by reverse-transcription of RNA.

When an RNA preparation step is included in the disclosed methods, the method of RNA preparation can be any method of RNA preparation that produces enzymatically manipulatable mRNA. For example, the RNA can be isolated by using the guanidinium isothiocyanate-ultracentrifugation method, the guanidinium and phenol-chloroform method, the lithium chloride-SDS-urea method or poly A+/mRNA from tissue lysates using oligo(dT) cellulose method, e.g., see Schildkraut et al., *J. Mol. Biol.* 4, 430-433 (1962); Chomczynski and Sacchi, *Anal. Biochem.* 162:156 (1987); Auffray and Rougeon, *Eur. J. Biochem.* 107:303-314 (1980); Aviv and Leder, *Proc. Natl. Acad. Sci. USA* 69, 1408-1412 (1972); and Sambrook et al., Selection of poly A+ RNA in "Molecular Cloning", Vol. 1, 7.26-7.29 (1989).

RNA can be isolated from any desired cell or cell type and from any organism, including mammals, such as mouse, rat, rabbit, dog, cat, monkey, and human, as well as other non-mammalian animals, such as fish or amphibians, as well as plants and even prokaryotes, such as bacteria. Thus, the DNA used in the method can also be from any organism, such as that disclosed for RNA.

Generation of cDNA

In some embodiments, disclosed methods involve cDNA preparation. The cDNA preparation step may be performed far removed from the actual amplification step, for example, in another laboratory, or at a much earlier time; however, in some embodiments the preparation of the cDNA may occur in conjunction with the amplification step of the methods.

When a cDNA preparation step is included in the disclosed methods, the method of cDNA preparation can be any method of cDNA preparation that produces enzymatically manipulatable cDNA. For example, the cDNA can be prepared by using, for example, random primers, poly-d(T) oligos, or NVd(T) oligos. For the purpose of data normalization, an equal amount of total RNA is typically used for cDNA synthesis. Many examples exist of performing reverse transcription to produce cDNA for use in PCR, including the following: Glisin et al., *Biochemistry* 13:2633-7 (1974); Ullrich et al., *Science* 196:1313 (1977); Chirgwin et al., *Biochemistry* 18:5294-9 (1979); Faulkner-Jones et al., *Endocrinol.* 133:2962-2972 (1993); and Gonda et al., *Mol. Cell Biol.* 2:617-624 (1982).

Reverse transcriptases from any source (native or recombinant) may be used in the practice of the present disclosure. Suitable reverse transcriptases include, but are not limited to, those from Moloney murine leukemia virus (M-MLV), human T-cell leukemia virus type I (HTLV-I), bovine leukemia virus (BLV), Avian Sarcoma Leukemia Viruses (ASLV) including Rous Sarcoma Virus (RSV) and Avian Myeloblastosis Virus (AMV), human immunodeficiency virus (HIV), cauliflower mosaic virus, *Saccharomyces, Neurospora, Drosophila*, primates, and rodents. See, for example, U.S. Pat. Nos. 4,663,290 and 6,063,600; Grandgenett et al., Proc. Nat. Acad. Sci. (USA) 70:230-234 (1973), Gerard, *DNA* 5:271-279 (1986), Kotewicz et al., *Gene* 35:249-258 (1985), Tanese et al., *Proc. Natl. Acad. Sci. (USA)* 82:4944-4948 (1985), Roth et al., *J. Biol. Chem.* 260:9326-9335 (1985), Michel et al., *Nature* 316:641-643 (1985), Akins et al., *Cell* 47:505-516 (1986) and *EMBO J.* 4:1267-75 (1985), and Fawcett, *Cell* 47:1007-1015 (1986); Shinnick et al., *Nature* 293:543-548 (1981); Seiki et al., *Proc. Natl. Acad. Sci. USA* 80:3618-3622 (1983); Rice et al., *Virology* 142:357-77 (1985); Schwartz et al., *Cell* 32:853-869 (1983); Larder et al., *EMBO J.* 6:3133-3137 (1987); Farmerie et al., *Science* 236:305-308 (1987); Barr et al., *Biotechnology* 5:486-489 (1987)); Tanese et al., *J. Virol.* 59:743-745 (1986); Hansen et al., *J. Biol. Chem.* 262:12393-12396 (1987); Sonigo et al., *Cell* 45:375-85 (1986); Takatsuji et al., *Nature* 319:240-243 (1986); Toh et al., *Nature* 305:827-829 (1983)); Alexander et al., *J. Virol.* 61:534-542 (1987); and Yuki et al., *Nucl. Acids Res.* 14:3017-3030 (1986).

Fragmentation

In embodiments wherein the samples comprise nucleic acids, target nucleic acids may be sheared or otherwise randomly fragmented (e.g., mechanically, enzymatically or with a chemical agent such as, for example, iron-EDTA sodium bisulfite or hydrazine). In embodiments wherein the target nucleic acids are DNA, the random shearing or fragmentation can cause single and/or double-stranded breaks in the DNA. Fragmenting only one strand of double stranded DNA may be achieved by random nicking by a chemical agent or an endonuclease such as DNAase I or micrococcal nuclease.

In some embodiments, target nucleic acids may be non-randomly fragmented. In embodiments wherein the nucleic acid targets are DNA, non-random fragmentation can be accomplished through treatment with restriction enzymes to completely digest or partially digest a DNA sample. The restriction enzymes can be methylation-sensing or non-sensing restriction enzymes. Since restriction enzymes cleave at predictable sites (e.g., at or near the fixed positions of restriction enzyme recognition sites in the DNA sample in the genome), restriction digests result in a non-random fragmentation of the DNA sample. In some embodiments, a partial digestion reaction is accomplished by preventing an enzyme from cleaving at every recognition sequence contained in a DNA sample in the appropriate methylation state. In some embodiments, partial digestions are accomplished by limiting the amount of enzyme added to the digestion reaction or limiting the amount of time the reaction is carried out. In addition, salinity, pH, temperature, pressure and other environmental parameters can be altered to prevent a digestion from progressing to completion. As a result of either full or partial enzyme digestions a fragmented population of genomic DNA with defined sequence ends, such as sticky ends or blunt ends, may be obtained.

Tagging

How the target is normalized is equally as important as the realization that capping maximal representation improves sequencing quality. In embodiments of the invention, a given target is bound to a tag that is capable of stably binding to a complementary capture moiety. In some embodiments of the invention, the tags are site-specific. In other embodiments of the invention, the tags are non-site-specific. In some embodiments, the tags are terminal. In embodiments where the targets are polynucleotides, terminal tags may be either at the 5' or 3' end of the molecule. In some embodiments of the invention, the targets are members of a library or are fragments of members of a library. Each set of library targets or fragments is bound to a unique polynucleotide tag that is at least partially single-stranded and is capable of hybridizing to a complementary sequence in a capture moiety. In some embodiments of the invention, tags comprise part of the common adaptor sequences that are bound to fragmented template DNA for NGS sequencing platforms. Methods of tagging targets that may be applicable in some embodiments of the invention have been previously described. See, for example, U.S. Pat. Nos. 5,652,128; 5,262,536; 5,969,784; 6,480,791; 6,773,886; and U.S. pre-grant publications 2005/0153333 and 2010/0317064; and references therein.

In some embodiments, multiple samples are obtained, targets isolated and tagged in a sample-specific manner, and then the differentially tagged targets from multiple samples are pooled. In some embodiments, the tags (e.g., appended oligonucleotides sequences) are identical for all targets in a particular sample and unique to the sample being assessed. In some embodiments, the tags are unique to a particular target or group of targets in a particular sample (i.e., inter-sample differential tagging) and are identical across multiple samples. In some embodiments, the tags are identical for all targets in a particular sample and unique for each sample in a plurality of samples. In some embodiments, tags may comprise proteins or polypeptides capable of binding to or interacting with another polypeptide such as an antibody.

In some embodiments, tags comprise at least two domains: a first domain comprising an identifying feature unique to the sample or target to which it is added/attached, and a second binding domain capable of binding to a capture moiety. The unique identifying feature allows multiplexing of samples such that multiple mixed samples can be simultaneously analyzed or processed. Methods of multiplexed DNA sequencing to which embodiments of the present invention may be adapted have been described previously; see, for example, U.S. Pat. No. 6,480,791 and U.S. pre-grant publication 2010/0113283.

The tag domains may, but need not, overlap. In some embodiments, the identifying feature is a polynucleotide sequence, and the binding domain is a polynucleotide sequence comprising a hybridization domain. In some embodiments, the identifying feature unique to the sample or target and the hybridization domain may comprise the same nucleotide sequence (i.e., a single nucleotide sequence that can serve as both a unique identifier and that can stably hybridize with a corresponding sequence under reasonable reaction conditions). The unique identifying feature may alternatively be referred to as "zip codes" or "barcodes". Inter-sample or intra-sample differentially tagged targets may be mixed, amplified and distinguished using the unique identifying features found within the tags attached to the targets prior to processing. Thus, embodiments of the invention allow one to sequence a variety of nucleic acid targets across a variety of samples at the same time.

Those of skill in the art will appreciate that multiplexing imparts a significant advantage to embodiments of the present invention. Multiplex samples and/or targets may be handled in parallel, which allows all subsequent processing and analysis (e.g., sequencing) to be conducted in parallel. For example, multiplexing significantly increases the rate of DNA sequencing reactions, e.g., from hundreds to thousands of bases per hour. In embodiments of the invention, the number of samples that can be multiplexed for parallel analysis may range from 5-10, 10-100, 100-500 or more.

Tagging may occur by protocols well-known to those of skill in the art, including covalent attachment, ionic attachment, ligation and PCR amplification of target sequences in which the PCR primers comprise a barcode, sequencing primer sites, an adaptor or spacer at the 5'-end of the primer and the capture tag sequence. See, for example, U.S. Pat. No. 8,039,214; U.S. pre-grant publication 2005/0153333; and U.S. pre-grant publication 2004/0110191; and references disclosed therein). The tags may be DNA or RNA, and can include base modifications and non-natural bases as previously described. See, for example, U.S. pre-grant publication 2012/0142004. The tags have sufficient length such that they are ably to stably bind (e.g., hybridize) with a complementary component or sequence under reasonable reaction conditions (temperature, pH, salt, etc.), yet are also capable of dissociating in a controlled and reproducible manner. In some embodiments, the tags comprise a feature (e.g., nucleotide sequence), that is sufficiently unique to ensure that differentially tagged targets from multiple samples can be pooled, processed, and the targets correlated with the samples from which they originated post-processing. In some embodiments, the tags are polynucleotides approximately 35 base pairs in length. In some embodiments, the tags are approximately 23-35 base pairs in length. In some embodiments, the tags are approximately 15-23 base pairs in length.

Capture Tag and Capture Moiety Preparation

Capture tags and capture moieties of the present disclosure may be prepared by any of a variety of methods (see, e.g., Sambrook et al., "*Molecular Cloning: A Laboratory Manual*", 1989, 2$^{nd}$ Ed., Cold Spring Harbour Laboratory Press: New York, N.Y.; "*PCR Protocols: A Guide to Methods and Applications*", 1990, Innis (Ed.), Academic Press: New York, N.Y.; Tijssen "*Hybridization with Nucleic Acid Probes—Laboratory Techniques in Biochemistry and Molecular Biology (Parts I and II)*", 1993, Elsevier Science; "*PCR Strategies*", 1995, Innis (Ed.), Academic Press: New York, N.Y.; and "*Short Protocols in Molecular Biology*", 2002, Ausubel (Ed.), 5$^{th}$ Ed., John Wiley & Sons: Secaucus, N.J.). Capture tags and capture moieties may be single- or double-stranded, and may be comprised of DNA, RNA, proteins, or any combination thereof.

Capture tags and capture moieties may be prepared by chemical techniques well-known in the art, including, e.g., chemical synthesis and polymerization based on a template as described, e.g., in Narang et al., *Meth. Enzymol.* 68:90-98 (1979); Brown et al., *Meth. Enzymol.* 68: 109-151 (1979); Belousov et al., *Nucleic Acids Res.* 25:3440-3444 (1997); Guschin et al., *Anal. Biochem.* 250:203-211 (1997); Blommers et al., *Biochemistry* 33:7886-7896 (1994); Frenkel et al., *Free Radic. Biol. Med.* 19:373-380 (1995); and U.S. Pat. No. 4,458,066.

In some embodiments, the capture tags are prepared such that they comprise a hybridization region that is at least partially single stranded. The hybridization region itself comprises a motif (i.e., nucleotide sequence) that corresponds with and is capable of binding (e.g., hybridizing) to a corresponding motif in an appropriate designed capture moiety. Methods of generating single stranded polynucleotides adaptable for use in the present invention are known in the art (see, e.g., U.S. Pat. No. 5,066,584; U.S. Pat. No. 5,518,900; and U.S. Pre-grant publication 2010/0331193).

In some embodiments, capture tags and capture moieties may be prepared using an automated, solid-phase procedure based on the phosphoramidite approach. In such methods, each nucleotide is individually added to the 5'-end of the growing oligonucleotide chain, which is attached at the 3'-end to a solid support. The added nucleotides are in the form of trivalent 3'-phosphoramidites that are protected from polymerization by a dimethoxytriyl (or DMT) group at the 5'-position. After base-induced phosphoramidite coupling, mild oxidation to give a pentavalent phosphotriester intermediate and DMT removal provides a new site for oligonucleotide elongation. The oligonucleotides are then cleaved off the solid support, and the phosphodiester and exocyclic amino groups are deprotected with ammonium hydroxide. These syntheses may be performed on oligo synthesizers such as those commercially available from Perkin Elmer/Applied Biosystems, Inc. (Foster City, Calif.), DuPont (Wilmington, Del.) or Milligen (Bedford, Mass.). Alternatively, oligonucleotides can be custom made and ordered from a variety of commercial sources well-known in the art, including, for example, the Midland Certified Reagent Company (Midland, Tex.), ExpressGen, Inc. (Chicago, Ill.), Operon Technologies, Inc. (Huntsville, Ala.), and many others.

Purification, where necessary or desirable, may be carried out by any of a variety of methods well-known in the art. For example, purification of oligonucleotides is typically performed either by native acrylamide gel electrophoresis, by anion-exchange HPLC, e.g., see Pearson and Regnier, *J. Chrom.* 255:137-149 (1983) or by reverse phase HPLC, e.g., see McFarland and Borer, *Nucleic Acids Res.* 7:1067-1080 (1979).

The sequence of the moieties and tags can be verified using any suitable sequencing method including, but not limited to, chemical degradation, e.g., see Maxam and Gilbert, *Methods of Enzymology*, 65:499-560 (1980), Sanger sequencing, NGS sequencing, matrix-assisted laser desorption ionization time-of-flight (MALDI-TOF) mass spectrometry, e.g., see Pieles et al., *Nucleic Acids Res.* 21:3191-

3196 (1993), and mass spectrometry following a combination of alkaline phosphatase and exonuclease digestions, e.g., see Wu and Aboleneen, *Anal. Biochem.* 290:347-352 (2001).

The present disclosure encompasses modified versions of capture tags and capture moieties that perform as equivalents in accordance with the methods of the present disclosure. These modifications may be accomplished using any of several means known in the art. Non-limiting examples of such modifications include methylation, "caps", substitution of one or more of the naturally occurring nucleotides with an analog, and internucleotide modifications such as, for example, those with uncharged linkages (e.g., methyl phosphonates, phosphotriesters, phosphoroamidates, carbamates, etc.), or charged linkages (e.g., phosphorothioates, phosphorodithioates, etc.). Modified oligonucleotide may also be derivatized by formation of a methyl or ethyl phosphotriester or an alkyl phosphoramidate linkage. Furthermore, the capture tags and moieties of the present disclosure may also be modified with a label.

Labeling of Capture Tags and Moieties

In some embodiments, capture tags and moieties may be labeled with a detectable agent to facilitate sorting and/or normalization control of targets. The role of a detectable agent is to allow visualization and detection of target sequences to which the agents are attached. In some embodiments, different targets in the same sample may be differentially or uniquely tagged such that each target (or selected group of targets) comprises a tag with a different detectable agent. In some embodiments, the same target within different samples (e.g., libraries comprised of sequences from different patients) may be tagged such that the target comprises an identical detectable agent in each sample. Preferably, the detectable agent is selected such that it generates a signal which can be measured and whose intensity is related (e.g., proportional) to the amount of target present. Thus, the amount of target present can be quantitated and subsequently capped where necessary within a predetermined range applicable to a given sequencing platform.

The association between the oligonucleotide and the detectable agent can be covalent or non-covalent. Labeled detection primers can be prepared by incorporation of or conjugation to a detectable moiety. Labels can be attached directly to the nucleic acid sequence or indirectly (e.g., through a linker). Linkers or spacer arms of various lengths are known in the art and are commercially available, and can be selected to reduce steric hindrance, or to confer other useful or desired properties to the resulting labeled molecules, e.g., see Mansfield et al., *Mol. Cell Probes* 9:145-156 (1995).

Various methods for labeling nucleic acid molecules are known in the art. For a review of labeling protocols, label detection techniques, and recent developments in the field, see, for example, Kricka, *Ann. Clin. Biochem.* 39:114-129 (2002); van Gijlswijk et al., *Expert Rev. Mol. Diagn.* 1:81-91 (2001); and Joos et al., *J. Biotechnol.* 35:135-153 (1994). Standard nucleic acid labeling methods include: incorporation of radioactive agents, direct attachments of fluorescent dyes (Smith et al., *Nucl. Acids Res.* 13:2399-2412 (1985)) or of enzymes (Connoly and Rider, *Nucl. Acids. Res.* 13:4485-4502 (1985)); chemical modifications of nucleic acid molecules making them detectable immunochemically or by other affinity reactions, e.g., see Broker et al., *Nucl. Acids Res.* 5:363-384 (1978); Bayer et al., *Methods of Biochem. Analysis* 26:1-45 (1980); Langer et al., *Proc. Natl. Acad. Sci. USA* 78:6633-6637 (1981); Richardson et al., *Nucl. Acids Res.* 11:6167-6184 (1983); Brigati et al., *Virol.* 126:32-50 (1983); Tchen et al., *Proc. Natl. Acad. Sci. USA* 81:3466-3470 (1984); Landegent et al., *Exp. Cell Res.* 15:61-72 (1984); and Hopman et al., *Exp. Cell Res.* 169:357-368 (1987); and enzyme-mediated labeling methods, such as random priming, nick translation, PCR and tailing with terminal transferase. For a review on enzymatic labeling, see, e.g., Temsamani and Agrawal, *Mol. Biotechnol.* 5:223-232 (1996). More recently developed nucleic acid labeling systems include, but are not limited to: ULS (Universal Linkage System), which is based on the reaction of monoreactive cisplatin derivatives with the N7 position of guanine moieties in DNA (Heetebrij et al., *Cytogenet. Cell. Genet.* 87:47-52 (1999)), psoralen-biotin, which intercalates into nucleic acids and upon UV irradiation becomes covalently bonded to the nucleotide bases (Levenson et al., *Methods Enzymol.* 184:577-583 (1990); and Pfannschmidt et al., *Nucleic Acids Res.* 24:1702-1709 (1996)), photoreactive azido derivatives (Neves et al., *Bioconjugate Chem.* 11:51-55 (2000)), and DNA alkylating agents (Sebestyen et al., *Nat. Biotechnol.* 16: 568-576 (1998)).

It will be appreciated that any of a wide variety of detectable agents can be used in the practice of the present disclosure. Suitable detectable agents include, but are not limited to, various ligands, radionuclides (such as, for example, $^{32}P$, $^{35}S$, $^{3}H$, $^{14}C$, $^{125}I$, $^{131}I$, and the like); fluorescent dyes; chemiluminescent agents (such as, for example, acridinium esters, stabilized dioxetanes, and the like); spectrally resolvable inorganic fluorescent semiconductor nanocrystals (i.e., quantum dots), metal nanoparticles (e.g., gold, silver, copper and platinum) or nanoclusters; enzymes (such as, for example, those used in an ELISA, e.g., horseradish peroxidase, beta-galactosidase, luciferase, alkaline phosphatase); colorimetric labels (such as, for example, dyes, colloidal gold, and the like); magnetic labels (such as, for example, Dynabeads™); and biotin, dioxigenin or other haptens and proteins for which antisera or monoclonal antibodies are available.

Pooling

As described above, embodiments of the invention are capable of normalizing targets across multiple targets by tagging the targets with sample-specific identifying features. In some embodiments, this allows the samples to be pooled immediately after tagging, which provides a significant advantage in efficiency by consolidation of subsequent processing and materials. Samples may be pooled at any stage after tagging. In practice, however, maximum efficiency is derived by pooling the samples as early as possible in any given multistep protocol.

In some embodiments of the invention, it is necessary to pool equal quantities of DNA from individual samples. In such embodiments, DNA concentration in each of the individual samples is measured by ultraviolet (UV) light spectroscopy, providing a first quantification. Optionally, a second quantification step is performed using a fluorimetry technique with a DNA-specific dye (e.g., PicoGreen). Fluormetric DNA quantification techniques are known in the art. See, for example, Barcellos et al., *Am. J. Hum. Genet.*, 1997, 61:737-747; Germer et al., *Genome Res.*, 2000, 10:258-266; Breen et al., 2000, *Biotechniques*, 2000, 28:464-470; and Plomin et al., *Behav. Genet.*, 2002, 31:497-509. Each sample is then diluted to an exact concentration (e.g., 1 µg/µl to 1 ηg/µl). DNA concentration is then checked again using one of the aforementioned fluormetric techniques, and the concentration is adjusted if necessary. A final, optional step involves selecting two targets known to be present in each sample and then quantifying the amounts of those samples by quantitative real-time PCR, thus confirming the amenability of each sample to amplification. Equimolar amounts of each sample are then combined.

Normalization

Once targets are tagged, capture moieties are used to isolate the targets within a precisely controlled stoichiometry. The amount and type of capture moieties may be selected to both cap the absolute number or amount of given target that is isolated and to isolate only targets possessing a tag complementary to the capture moiety. Thus, the amount of capture moiety is the limiting factor that caps the isolation of over-abundant targets. This normalization protocol may be applied to an individual sample or across multiple pooled samples. For example, in some embodiments, samples are isolated, and targets within each sample are tagged in a sample-specific manner; in other words, the identifying feature of the tag is unique to each sample. The tagged and sample-specific targets are pooled for efficiency and economies of scale. After pooling, a set or predetermined amount of capture moieties can be added, wherein each of the sample-specific tags corresponds to a particular capture moiety, i.e., there is a capture moiety that binds only targets from sample 1, another that binds targets only from sample 2, etc. Thus, the amount of each particular capture moiety that is added can be used to normalize variation across the samples. For example, if the samples are libraries, and there are six copies of the target in library 1, three in library 2, and five in library 3, adding four of each sample-specific capture moieties would normalize the targets as follows: four copies from library 1, three copies from library 2, and four copies from library 3. Thus, high copy number variation between the different libraries is normalized in a manner dependent upon the calculated or approximately determined amount of sample-specific capture moiety.

As can be appreciated from the simplistic illustration above, the amount of capture moiety must be less than at least the amount or estimated amount of the most abundant target in the sample or samples to which it is capable of binding; otherwise normalization would not occur. Target copy numbers that exceed the amount of the capture moiety are not captured and, therefore, not processed. In other words, any extreme variation in excess of the capture moiety is normalized-out by the amount of the capture moiety. It is possible, in some embodiments of the invention, to calculate target abundance. Absolute quantification can be achieved by using a standard curve, constructed by amplifying known amounts of target DNA in a parallel set of reactions. Absolute quantification requires that the exact quantity of a standard is determined by independent means using spectrophotometry or an intercalating dye such as PicoGreen. In practice, however, the amount of a given target necessary for subsequent processing (e.g., sequencing) is far below the amount of that target present in a sample. Theoretically, for example, only one copy of a target need be present, which can then be clonally amplified or directly processed in a single-molecule NGS protocol. The amount of capture moiety can be in great excess of the lower copy number transcripts. Thus, capture moiety amounts can be arbitrarily set within a range that is sufficient to isolate low copy number targets but below the maximum operational throughput of the downstream application (e.g., NGS sequencing). In some embodiments, e.g., in the case of HIV viral RNA capture, this target range of capture moiety per milliliter is 10 copies to 100 copies, or 100 copies to 1,000 copies, or 1,000 to 10,000 copies or up to 1,000,000 or more copies. If greater sensitivity for minority species is required, a higher limit is set, and if more samples are to be multiplexed and simultaneously measured, then a level around 10,000 may be used.

In some embodiments, samples are obtained from a plurality of subjects and all, or a selected group, of targets within a given sample attached to a tag with a motif that is specific for a particular capture moiety and unique to that sample. If the samples are pooled, control of the capture moieties allows a user to select only targets that correspond to the capture moiety of choice. By including only specific quantities of the capture moiety of choice (e.g., a quantity within an optimized input range for a given sequencing platform), any target in excess of those quantities will not be bound and can be eliminated from downstream processing or applications (e.g., sequencing). Inclusion of a unique identifying feature within the tags or the capture moieties allows the targets to be distinguished and correlated with their original sample after pooling. For example, in one embodiment, a capture moiety comprises a polynucleotide sequence and the corresponding tag comprises a sequence complementary to that sequence, such that the capture tag is capable of specifically hybridizing with the capture moiety. Capture moieties may be DNA or RNA, single- or double-stranded, or any combination thereof.

Capture moieties must be capable of binding to correspondingly tagged targets. In some embodiments of the invention, the capture tags and the capture moieties are polynucleotides. In such embodiments, the capture tags comprise a nucleotide sequence that is capable of hybridizing to a complementary sequence in the capture moiety. Hybridization is conducted under suitable hybridization conditions, which may vary in stringency as desired. Stringency of hybridization may be controlled by both temperature and salt concentration. For example, the conditions of hybridization to achieve selective hybridization may involve hybridization in high ionic strength solution (6×SSC or 6×SSPE) at a temperature that is approximately 12-25° C. below the Tm (the melting temperature at which half of the molecules dissociate from their hybridization partners). The temperature and salt conditions may be determined empirically in preliminary experiments in which samples of reference DNA immobilized on filters are hybridized to a labeled nucleic acid of interest and then washed under conditions of different stringencies. Hybridization temperatures are typically higher for DNA-RNA and RNA-RNA hybridizations. The conditions can be used as described above to achieve stringency, or as is known in the art. (Sambrook et al., Molecular Cloning: A Laboratory Manual, 2nd Ed., Cold Spring Harbor Laboratory, Cold Spring Harbor, N.Y., 1989; Kunkel et al. *Methods Enzymol.* 1987:154: 367, 1987). Stringency of hybridization and washing, if desired, can be reduced accordingly as the degree of complementarity desired is decreased, and further, depending upon the G-C or A-T richness of the tag/capture moiety. Exemplary low stringency conditions include hybridization with a buffer solution of about 30% to about 35% formamide, about 1 M NaCl, about 1% SDS (sodium dodecyl sulphate) at about 37° C., and a wash in about 1× to about 2×SSC (20×SSC=3.0 M NaCl/0.3 M trisodium citrate) at about 50° C. to about 55° C. Exemplary moderate stringency conditions include hybridization in about 40% to about 45% formamide, about 1 M NaCl, about 1% SDS at about 37° C., and a wash in about 0.5× to about 1×SSC at abut 55° C. to about 60° C. Likewise, stringency of hybridization and washing, if desired, can be increased accordingly as the desired level of homology is increased, and further, depending upon the G-C or A-T richness of any area wherein high homology is desired, all as known in the art. The duration of hybridization is generally less than about 24 hours, usually about 4 to about 12 hours.

In some embodiments, the capture moieties comprise polynucleotides. The polynucleotides may be approximately 100-90, 90-80, 80-70, 70-60, 60-50, 50-40, 40-30 or 30-20 base pairs in length. Polynucleotide capture moieties may comprise a sequence or structure that is capable of binding to a complementary sequence or structure in a capture tag. In some embodiments, this sequence or structure is between 10 and 100 nucleotides in length, or between about 12 and 50 nucleotides in length, and is capable of forming a hybrid with complementary sequence in a capture tag such that it is sufficiently stable under stringent hybridization conditions. The hybrids may comprise RNA:RNA, RNA:DNA, or DNA:DNA duplex molecules or duplex molecules containing analogs of these nucleic acids. It will be appreciated that substantially corresponding tags and capture moieties of the invention can vary from strict complementarity and still hybridize. Variation from a canonical complementary nucleic acid may be stated in terms of a percentage of identical bases within the sequence or the percentage of perfectly complementary bases between the capture moiety and the tag. For example, in some embodiments, tags and capture moieties are substantially complementary and capable of hybridizing if they are 100% to 80% complementary, or have 0-2 base mismatches in a 10 nucleotide sequence.

Attachment to Solid Supports

In some embodiments, the capture moieties are affixed directly to a solid support. A wide variety of solid supports may be used, and it is not intended that the invention be limited to the use of any particular type of solid support. Similarly, it is not intended that the manner in which the capture moieties are directly or indirectly attached to the solid support should be limiting in any way.

In some embodiments, the capture moieties may comprise an array (e.g., a chip) of oligomers. Detailed methods for making and using arrays comprising polymeric nucleobase structures (e.g., nucleic acid, modified nucleic acids, nucleic acid analogs, or chimeric structures) are well-known in the art and are described in many sources. See, e.g., Ausubel et al. (eds.), Current Protocols in Molecular Biology, Chapter 22, "Nucleic Acid Arrays," John Wiley & Sons, Inc., New York [1994]; and M. Schena, (ed.), Microarray Biochip Technology, BioTechnique Books, Eaton Publishing, Natick, Mass. [2000]. Any methods for the synthesis and use of nucleic acids, modified nucleic acids and nucleic acid analogs with solid supports, and more specifically arrays, can be used.

Because the location, tag-binding sequence and amount of each support-bound capture moiety are known, and because each target tag can comprise unique identifying features, arrays can be used to simultaneously detect, identify and/or quantitate the presence or amount of one or more target sequences and the sample source of those sequences. For example, a target tag sequence can be captured by the complementary capture moiety on the array surface and then the complex containing the target sequence can be detected. Since the sequence of the capture moiety corresponding to the tag is known at each location on the surface of the array, the binding of a tagged target can be directly detected, identified and/or quantitated by determining the location of a detectable signal generated on the array.

In one embodiment, the capture moieties can be synthesized on the surface in a manner suitable for deprotection but not cleavage from the synthesis support (see, e.g., Weiler et al., *Nucl. Acids Res.*, 25(14):2792-2799 (1997)). In still another embodiment, one or more capture moieties can be covalently linked to a surface by the reaction of a suitable functional group on the capture moiety or tag with a functional group of the surface (see, e.g., Geiger et al., *Nucleosides & Nucleotides* 17(9-11):1717-1724 (1998)). This method is advantageous since the capture moieties immobilized on the surface can be highly purified and attached using a defined chemistry, thereby possibly minimizing or eliminating non-specific interactions.

Methods for the chemical attachment of capture moieties to solid support surfaces can involve the reaction of a nucleophilic group, (e.g., an amine or thiol) of the capture moiety or tag to be immobilized, with an electrophilic group on the solid support surface. Alternatively, the nucleophile can be present on the support and the electrophile (e.g., activated carboxylic acid) can be present on the capture moiety. In some embodiments, such capture moieties may be attached to a solid support by click chemistry. In some embodiments, such moieties are attached via a 1,3-cycloaddition of an azide with an alkyne, optionally in the presence of a copper catalyst. Methods of using click chemistry are known in the art and include those described by Rostovtsev et al., Angew. Chem. Int. Ed. 2002, 41: 2596-99 and Sun et al., Bioconjugate Chem., 2006, 17: 52-57.

In some embodiments of the invention, capture probes are directly attached to solid substrates via standard N-ethyl-N'-(dimethylaminopropyl)carbodiimide/N-hydroxysuccinimide (EDC/NHS) amine coupling procedures. Amine coupling introduces N-hydroxysuccinimide esters into the surface matrix by modification of the carboxymethyl groups with a mixture of N-hydroxysuccinimide (NHS) and N-ethyl-N'-(dimethylaminopropyl)-carbodiimide (EDC). These esters then react spontaneously with amines and other nucleophilic groups on the capture moiety to form covalent links. This is a highly stable and common surface functionalization technique.

Conditions suitable for the immobilization of a capture moiety are widely known in the art. The immobilization reaction to a solid support is analogous to a labeling reaction, where the label is substituted with the surface to which the polymer is to be linked. It is not intended that the invention be limited to any particular immobilization chemistry or method. In some embodiments, capture moieties are non-covalently associated with a solid substrate. In some embodiments, a capture moiety is non-covalently attached to a solid substrate in that it is embedded within the substrate surface (e.g., is intercalated within a polymeric matrix at the surface). In some embodiments, a capture moiety is non-covalently attached to a substrate surface by way of an interaction selected from the group consisting of hydrophobic interactions, electrostatic interactions, polar interactions, affinity interactions, metal coordination, hydrogen bonding, pi-stacking interactions, van der Waals interactions, magnetic interactions, dipole-dipole interactions, and/or combinations thereof. For example, in some embodiments, a capture moiety is attached to a solid surface by way of an interaction between complementary affinity tags, one of which is attached (e.g., covalently bound to) the solid surface (whether directly or indirectly), and one of which is attached to the capture moiety. Exemplary affinity tag pairs include, but are not limited to, epitope/antibody, biotin/avidin, biotin/streptavidin, biotin/neutravidin, glutathione-S-transferase/glutathione, maltose binding protein/amylase, histidine/nickel-nitrolotriaceteic acid (Ni-NTA), maltose binding protein/maltose, and/or complementary single-stranded nucleic acids. Examples of suitable epitopes which may be used for epitope/antibody binding pairs include, but are not limited to, HA, FLAG, c-Myc, glutathione-S-transferase, $His_6$, GFP, DIG, biotin and avidin. Antibodies (e.g., monoclonal antibodies, polyclonal antibodies, and/or antigen-binding fragments thereof) which bind to these epitopes are well known in the art.

Numerous types of solid supports derivatized with amino groups, carboxylic acid groups, isocyantes, isothiocyanates and malimide groups are commercially available. Non-limiting examples of suitable solid supports include chips of any type (e.g., arrays), membranes, glass, controlled pore glass, polystyrene particles (beads), magnetic beads, capillary tubes, silica and gold nanoparticles. In some embodiments, the solid supports may be open wells or closed flowcells, wherein the solution comprising the targets is at least partially constrained by a solid substrate. In other embodiments, the solid supports may be functionalized particles, wherein the solid substrate is surrounded by a target-comprising solution. Small particles have the advantage of providing high surface area for binding coupled with ease of use in embodiments comprising centrifugation or magnetic separation. Furthermore, particles may be sized such that they are amenable to automated preparation and sequencing. In some embodiments of the invention, spherical particle substrates may have a diameter less than 100 µm, 10 µm, 1 µm, 500 µm, 100 µm, 50 ηm or less. In one embodiment of the invention, the solid supports are 100 ηm by 1 µm by 1 µm in dimension. In one embodiment of the invention, paramagnetic micron-scale beads are used.

Universal Probes

In preferred embodiments, capture moieties bind (e.g., hybridize) to capture tags in solution. In other words, the capture moieties, and hence normalization control, is not effected on a solid surface. In such embodiments, the capture moieties are subsequently and indirectly captured on a solid support via a universal probe sequence capable of binding all the capture moieties in a given sample or pooled set of sample irrespective of the target to which the capture moiety is bound. Thus, selection of the type and amount of capture moieties may be used as normalization controls in solution to select particular species of targets and cap the amount of the targets as necessary for downstream processing. Those of skill in the art will appreciate that effecting normalization control in solution is a significant advantage of particular embodiments of the invention. It avoids the need for strict quality control associated with the quantitative attachment of capture moieties to solid supports. In some embodiments of the invention, the universal probe sequences are oligonucleotides capable of binding to complementary sequence present in the capture moieties. Methods for using universal oligonucleotide sequences are known in the art; see, for example, U.S. Pat. Nos. 6,480,791 and 7,176,007. Universal probes may be at least 5, at least 10, at least 15, at least 20, at least 25, at least 30, at least 35, at least 45 or at least 50 nucleotides in length.

Universal probe sequences may be bound to a solid support as described for capture moieties above. In some embodiments, the universal probes may be attached to a solid support at their 5' ends by a flexible linker (see, e.g., Adessi et al., *Nucleic Acids Res.*, 2000, 28:e87; Fedurco et al., *Nucleic Acids Res.*, 2006, 34:e22). In some embodiments, solid supports comprise at least 1, at least 2, at least 3, at least 4, at least 5, at least 6, at least 7, at least 8, at least 9, or at least 10 distinct unique universal probe sequences capable of binding at least at least 1, at least 2, at least 3, at least 4, at least 5, at least 6, at least 7, at least 8, at least 9, or at least 10 different capture moieties. In some embodiments, a single solid support is associated with at least 1, at least 2, at least 3, at least 4, at least 5, at least 6, at least 7, at least 8, at least 9, at least 10, at least 20, at least 50, at least 100, at least 1000 or more identical universal probes. In some embodiments of the invention, the universal probe sequence may be present on a solid support in great excess of all the targets (e.g., library fragments) or capture moieties present in a sample or pooled set of samples. Thus, normalization control can be mediated by careful selection of the quantity and type of the capture moieties. In some embodiments, targets/capture moieties and universal probes are present at a ratio of about 0.001:1, 0.005:1, 0.01:1, about 0.02:1, about 0.05:1, about 0.1:1, about 0.2:1, about 0.3:1, about 0.4:1, about 0.5:1, about 0.6:1, about 0.7:1, about 0.8:1, about 0.9:1, about 1:1, about 1:2, about 1:3, about 1:4, about 1:5, about 1:6, about 1:7, about 1:8, about 1:9, about 1:10, about 1:20, about 1:50, about 1:100, or about 1:1000.

In embodiments wherein universal probe sequences are bound to a solid support, the capture moieties may be bi-functional capture oligonucleotides. Bi-functional capture moieties or oligonucleotides comprise a first part that binds to the capture tags and a second part that binds to universal probes attached to the solid support. In some embodiments, one or both parts are terminal, i.e., located at the 5' and/or 3' end of the bi-functional capture moieties. In some embodiments of the invention, the first part is an oligonucleotide sequence capable of binding or hybridizing to a complementary sequence found in all capture tags bound to targets in a given sample or set of samples. It will be appreciated that the sequence, amount and hybridization conditions of the first part controls the number of targets that are bound in a given reaction. In some embodiments of the invention, the first part comprises an antibody capable of specifically binding a polypeptide appended to the targets. In some embodiments of the invention, the second part of the bi-functional capture moieties or oligonucleotides comprises a universal hybridization sequence capable binding to universal probes under appropriate conditions. In some embodiments the capture moieties may be multi-functional capture oligonucleotides (e.g., with 3 or more parts such as those found in branched DNA or bDNA structures and the like).

Those of skill in the art will appreciate that the use of bi-functional capture moieties or oligonucleotides provides several advantages. For example, quality control of normalization is achieved separately from the solid support, which enhances specificity and sensitivity of target/capture moiety binding. It is also easier to manufacture a solid support with fixed universal probes than with heterogeneous capture moieties at predetermined levels. As mentioned, the exact binding capacity of the solid substrates is largely immaterial as long as it is higher than the desired library output.

Universal probes may be engineered to comprise an oligonucleotide sequence complementary to a sequence in the bi-functional capture moieties. Additionally, either the capture tags or the bi-functional capture moieties may comprise one or more universal bases. Universal bases can pair with more than one of the bases typically found in naturally occurring nucleic acids and can thus substitute for such naturally occurring bases in a duplex. The base need not be capable of pairing with each of the naturally occurring bases. For example, certain bases pair only or selectively with purines, or only or selectively with pyrimidines. Certain universal bases (fully universal bases) can pair with any of the bases typically found in naturally occurring nucleic acids and can thus substitute for any of these bases in duplex. The base need not be equally capable of pairing with each of the naturally occurring bases. If a probe mix contains probes that comprise (at one or more positions) a universal base that does not pair with all of the naturally occurring nucleotides, it may be desirable to utilize two or more universal bases at that position in the particular probe so that at least one of the universal bases pairs with A, at least one of the universal bases pairs with G, at least one of the universal bases pairs with C, and at least one of the universal bases pairs with T.

A number of universal bases are known in the art including, but not limited to, hypoxanthine, 3-nitropyrrole, 4-nitroindole, 5-nitroindole, 4-nitrobenzimidazole, 5-nitroindazole, 8-aza-7-deazaadenine, 6H,8H-3,4-dihydropyrimido[4,5-c][1,2]oxazin-7-one (P. Kong Thoo Lin. and D. M. Brown, *Nucleic Acids Res.*, 1989, 17, 10373-10383), 2-amino-6-methoxyaminopurine (D. M. Brown and P. Kong Thoo Lin, *Carbohydrate Research,* 1991, 216, 129-139), etc. Hypoxanthine is one fully universal base. Nucleosides comprising hypoxanthine include, but are not limited to, inosine, isoinosine, 2'-deoxyinosine, and 7-deaza-2'-deoxyinosine, 2-aza-2'deoxyinosine. Additional universal bases are known in the art as described, for example, in relevant portions of Loakes and Brown, *Nucleic Acids Res.* 22:4039-4043, 1994; Ohtsuka et al., *J. Biol. Chem.* 260(5):2605-2608, 1985; Lin, P. K. T. and Brown, D. M., *Nucleic Acids Res.* 20(19):5149-5152, 1992; Nichols et al., *Nature* 369(6480): 492-493, 1994; Rahmon and Humayun, *Mutation Research* 377 (2): 263-8, 1997; Berger et al., *Nucleic Acids Research,* 28(15): 2911-2914, 2000; Amosova et al., *Nucleic Acids Res.* 25 (10): 1930-1934, 1997; and Loakes, *Nucleic Acids Res.* 29(12):2437-47, 2001. The universal base may, but need not, form hydrogen bonds with an oppositely located base. The universal base may form hydrogen bonds via Watson-Crick or non-Watson-Crick interactions (e.g., Hoogsteen interactions).

In some embodiments of the invention, the universal probes can incorporate or serves as primers for the "sequencing-by-synthesis" reactions of NGS platforms. As described above, certain NGS platforms (such as 454 pyrosequencing and the Solexa/Illumina Genome Analyzer) sequence a dense array of DNA targets by iterative cycles of primed template extension and imaging-based data collection. A DNA polymerase incorporates fluorescently labeled nucleotides into the template. In certain embodiments of the invention, single-stranded universal probes of approximately 15-45 nucleotides in length may be spatially separated and immobilized on a solid support. The single-stranded universal probes can then bind single-stranded targets/capture moieties as part of the normalization protocol and also prime the targets/capture moieties for the DNA polymerase.

Washing

After tagged targets are bound to the capture moiety and the capture moiety is directly or indirectly bound to a solid support, a wash buffer is typically applied. The tagged and bound targets are washed under conditions to preserve the binding (e.g., hybridization), thereby removing all targets lacking a capture moiety partner and removing copies of the targets in excess of the amount of capture moiety, non-labeled targets (e.g., library fragments) and other nucleic acid or chemical contaminants. The pH and salt composition and concentration of the wash buffer can be varied according to the length of the targets and capture moieties, the extent of the binding between the tags and capture moieties, the nature of the binding between the tags and the capture moieties, binding conditions (e.g., hybridization conditions), etc. For example, ethanol exemplifies a wash buffer useful to remove excess detergent and salt. Washing may be repeated two, three, four or five or more times as necessary to ensure removal of unbound targets.

The qualities of suitable wash buffers are known to those of skill in the art. A suitable wash buffer should have a sufficiently high salt concentration (i.e., be of sufficiently high ionic strength) that the capture moiety and/or universal probe are not eluted off the solid support. In some embodiments, a suitable salt concentration is greater than about 0.2 M, but can be reduced when stronger forces bind the nucleic acid to the solid support. For example, a 10 mM Tris buffer, pH 8.0 can be used to wash nucleic acid bound to a solid support that contains multiple nucleic acid binding groups, and which resists elution under most commonly-used elution conditions (US 2005/0106589; US 2005/0106602). In some embodiments, a wash buffer has sufficiently high alcohol content, such as ethanol, such that the nucleic acid remains a precipitate attached to the solid support. A wash buffer solution can also be chosen so that impurities that are bound to DNA or solid phase carrier are dissolved. The pH and solute composition and concentration of the buffer solution can be varied according to the types of impurities which are expected to be present. For example, a suitable non-limiting set of wash buffers useful in the isolation of nucleic acid from viral particles includes: (I) 1.67 M guanidinium isothiocyanate, 33% isopropyl alcohol, 0.33% lauroylsarcosine, 0.033 M Tris HCl, pH 7.0; and (II) 70% ethanol, 10 mM KCl, 2 mM Tris pH 7.0, 0.2 mM EDTA, pH 8.0. Wash buffers can be of similar constitution to the buffer in which hybridization occurs.

Dissociation

In some embodiments of the invention, normalized targets are dissociated from the capture moieties and/or solid supports. Dissociation may be affected by changing the conditions under which the tagged targets are bound to the capture moieties. For example, temperature, salt and pH may be adjusted to conditions unfavorable to hybridization, as is well known to those of skill in the art. Reducing the concentration of salt to, for example, less than 0.2 M results in significantly reduced nucleic acid hybridization. Normalized targets may be dissociated from solid support by elution buffers. Buffers to elute nucleic acids bound to solid supports are known in the art, e.g., TE buffer (typically 10 mM Tris, 1 mM EDTA pH 7.5 to 8.0; U.S. Pat. No. 7,052,840), 0.1×TE pH 7.5-8.0, Tris-HCl (10 mM), EDTA (e.g., 0.1 mM pH 8.0; US 2005/0059024), Tris acetate (DeAngleis et al., *Nucleic Acids Res.* 1994; 23:4742-4743), potassium chloride buffer (1 mM KCl, 0.2 mM sodium citrate), sucrose (e.g., 20%), formamide (e.g., 70% or 100%; U.S. Pat. No. 6,534,262), formamide/EDTA (e.g., 70%/1 mM; see, e.g., U.S. Pat. No. 6,534,262), pyrrolidinone (e.g., 12%; U.S. Pat. No. 6,534,262) and nuclease-free water (see, e.g., U.S. Pat. No. 5,705,628, U.S. Pat. Nos. 5,898,071 and 6,534,262, published U.S. application No. 2005/0196856). Other elution buffers known in the art include, but are not limited to, 1 mM sodium citrate pH 6.4, which optionally can be pre-warmed, and is used to elute mRNA from poly(dT) beads (see e.g., U.S. Pat. No. 6,812,341). Other elution buffers also can be developed to suit particular binding conditions. For example, nucleic acid bound with high affinity to beads containing multiple nucleic acid binding groups can be eluted with buffers that contain an organic solvent, such as 5% DTT and salt, such as 0.75M NaCl (US 2005/0106589). The choice of buffer may also be influenced by the reactions to follow, e.g., the choice of sequencing protocol. In some embodiments, dissociation of the capture tags and capture moieties may be achieved by enzymatic cleavage or digestion.

It will be appreciated, however, that in certain embodiment of the invention, the normalized targets do not need to be dissociated from the capture moieties. The presently disclosed normalization protocols, particularly when applied to targets that are or have been made single-stranded, may be adapted to single-molecule template NGS platforms as discussed below. Either the capture tags or the capture moieties may incorporate amplification primer sequences, thereby forming a primed template. Alternatively, the universal probes may serve as amplification primers. If the primed template is immobilized in a spatially distributed manner, a DNA polymerase can be added to initiate an NGS reaction. In such platforms, the normalized targets may remain captured by the solid support Amplification Reaction Some embodiments of the invention require amplification of targets, e.g., tags may be incorporated into PCR primers used to amplify a library. Embodiments of the invention may also require amplification of targets following normalization. The basis of nucleic acid amplification are well-known in the art (see, for example, Kimmel and Berger, *Methods Enzymol.* 152: 307-316 (1987); Sambrook et al., "*Molecular Cloning: A Laboratory Manual*", 1989, $2^{nd}$ Ed., Cold Spring Harbour Laboratory Press: New York, N.Y.; "*Short Protocols in Molecular Biology*", Ausubel (Ed.), 2002, $5^{th}$ Ed., John Wiley & Sons: Secaucus, N.J.).

Such nucleic acid amplification methods include, but are not limited to, the Polymerase Chain Reaction (or PCR, described, for example, in "*PCR Protocols: A Guide to Methods and Applications*", Innis (Ed.), 1990, Academic Press: New York; "*PCR Strategies*", Innis (Ed.), 1995, Academic Press: New York; "*Polymerase chain reaction: basic principles and automation in PCR: A Practical Approach*", McPherson et al. (Eds.), 1991, IRL Press: Oxford; Saiki et al., *Nature* 324:163 (1986); and U.S. Pat. Nos. 4,683,195, 4,683,202 and 4,889,818); reverse transcriptase polymerase chain reaction (or RT-PCR, described in, for example, U.S. Pat. Nos. 5,322,770 and 5,310,652); emulsion PCR (Dressman et al., *Proc. Natl. Acad. Sci. USA,* 2003, 100:8817-8822); and solid-phase amplification (Fedurco et al., *Nucleic Acids Res.,* 2006, 34:e22).

The PCR (or polymerase chain reaction) technique is well-known in the art and has been disclosed, for example, in Mullis and Faloona, *Methods Enzymol.,* 155:350-355 (1987). In its simplest form, PCR is an in vitro method for the enzymatic synthesis of specific DNA sequences, using two primers that hybridize to opposite strands and flank the region of interest in the target DNA. A plurality of reaction cycles, each cycle comprising: a denaturation step, an annealing step, and a polymerization step, results in the exponential accumulation of a specific DNA fragment, see for example, "*PCR Protocols: A Guide to Methods and Applications*", Innis (Ed.), 1990, Academic Press: New York; "*PCR Strategies*", Innis (Ed.), 1995, Academic Press: New York; "*Polymerase chain reaction: basic principles and automation in PCR: A Practical Approach*", McPherson et al. (Eds.), 1991, IRL Press: Oxford; Saiki et al., *Nature* 324:163-166 (1986). The termini of the amplified fragments are defined as the 5' ends of the primers. Examples of DNA polymerases capable of producing amplification products in PCR reactions include, but are not limited to: *E. coli* DNA polymerase I, Klenow fragment of DNA polymerase I, T4 DNA polymerase, thermostable DNA polymerases isolated from *Thermus aquaticus* (Taq) which are available from a variety of sources (for example, Perkin Elmer), *Thermus thermophilus* (United States Biochemicals), *Bacillus stereothermophilus* (Bio-Rad), or *Thermococcus litoralis* ("Vent" polymerase, New England Biolabs). RNA target sequences may be amplified by reverse transcribing the mRNA into cDNA, and then performing PCR (RT-PCR), as described above. Alternatively, a single enzyme may be used for both steps as described in U.S. Pat. No. 5,322,770.

The duration and temperature of each step of a PCR cycle, as well as the number of cycles, are generally adjusted according to the stringency requirements in effect. Annealing temperature and timing are determined both by the efficiency with which a primer is expected to anneal to a template and the degree of mismatch that is to be tolerated. The ability to optimize the reaction cycle conditions is well within the knowledge of one of ordinary skill in the art. Although the number of reaction cycles may vary depending on the detection analysis being performed, it usually is at least 15, more usually at least 20, and may be as high as 60 or higher. However, in many situations, the number of reaction cycles may range from about 20 to about 40.

The denaturation step of a PCR cycle generally comprises heating the reaction mixture to an elevated temperature and maintaining the mixture at the elevated temperature for a period of time sufficient for any double-stranded or hybridized nucleic acid present in the reaction mixture to dissociate. For denaturation, the temperature of the reaction mixture is usually raised to, and maintained at, a temperature ranging from about 85° C. to about 100° C., usually from about 90° C. to about 98° C., and more usually about 90° C. to about 94° C. for a period of time ranging from about 3 to about 120 seconds, usually from about 5 to about 30 seconds. In some embodiments, the first cycle is preceded by an elongated denaturation step ranging from about 1 to 10 minutes, usually from about 2 to 5 minutes.

Following denaturation, the reaction mixture is subjected to conditions sufficient for primer annealing to template DNA present in the mixture. The temperature to which the reaction mixture is lowered to achieve these conditions is usually chosen to provide optimal efficiency and specificity, and generally ranges from about 45° C. to about 75° C., usually from about 50° C. to about 70° C., and more usually from about 53° C. to about 55° C. Annealing conditions are generally maintained for a period of time ranging from about 15 seconds to about 30 minutes, usually from about 30 seconds to about 1 minute.

Following annealing of primer to template DNA or during annealing of primer to template DNA, the reaction mixture is subjected to conditions sufficient to provide for polymerization of nucleotides to the primer's end in a such manner that the primer is extended in a 5' to 3' direction using the DNA to which it is hybridized as a template (i.e., conditions sufficient for enzymatic production of primer extension product). To achieve primer extension conditions, the temperature of the reaction mixture is typically raised to a temperature ranging from about 65° C. to about 75° C., usually from about 67° C. to about 73° C., and maintained at that temperature for a period of time ranging from about 15 seconds to about 20 minutes, usually from about 30 seconds to about 5 minutes. In some embodiments, the final extension step is followed by an elongated extension step ranging from ranging from about 1 to 10 minutes, usually from about 2 to 5 minutes.

The above cycles of denaturation, annealing, and polymerization may be performed using an automated device typically known as a thermal cycler or thermocycler. Thermal cyclers that may be employed are described in U.S. Pat.

Nos. 5,612,473; 5,602,756; 5,538,871; and 5,475,610. Thermal cyclers are commercially available, for example, from Perkin Elmer-Applied Biosystems (Norwalk, Conn.), Bio-Rad (Hercules, Calif.), Roche Applied Science (Indianapolis, Ind.), and Stratagene (La Jolla, Calif.).

In some embodiments, one or both of the PCR reactions are "kinetic PCR" (kPCR) or "kinetic RT-PCR" (kRT-PCR), which are also referred to as "real-time PCR" and "real-time RT-PCR," respectively. These methods involve detecting PCR products via a probe that provides a signal (typically a fluorescent signal) that is related to the amount of amplified product in the sample. Examples of commonly used probes used in kPCR and kRT-PCR include the following probes: TAQMAN® probes, Molecular Beacons probes, SCORPION® probes, and SYBR® Green probes. Briefly, TAQMAN® probes, Molecular Beacons, and SCORPION® probes each have a fluorescent reporter dye (also called a "fluor") attached to the 5' end of the probes and a quencher moiety coupled to the 3' end of the probes. In the unhybridized state, the proximity of the fluor and the quench molecules prevents the detection of fluorescent signal from the probe. During PCR, when the polymerase replicates a template on which a probe is bound, the 5'-nuclease activity of the polymerase cleaves the probe thus, increasing fluorescence with each replication cycle. SYBR® Green probes binds double-stranded DNA and upon excitation emit light; thus as PCR product accumulates, fluorescence increases.

In some embodiments, the PCR reaction is used in a "single-plex" PCR assay. "Single-plex" refers to a single assay that is not carried out simultaneously with any other assays. Single-plex assays include individual assays that are carried out sequentially.

In some embodiments, the PCR reaction is used in a "multiplex" PCR assay. The term "multiplex" refers to multiple assays that are carried out simultaneously, in which detection and analysis steps are generally performed in parallel.

In some embodiments, a first amplification step amplifies a region of a target gene. In some embodiments the amplification product is less than about 1500, 1400, 1300, 1200, 1100, 1000, 900, 800, 700, 600, 500, 400, 300, 250, 225, 200, 175 or 150 nucleotides long.

Sequencing

Nucleic acid sequencing is applicable to some embodiments of the invention. Nucleic acid sequencing, in its broadest sense, comprises determination of the identity of a nucleotide at a given position within an oligonucleotide or polynucleotide. In some embodiments, sequencing comprises detecting the differences of at least one nucleotide between two nucleic acids. Examples of techniques for detecting differences of at least one nucleotide between two nucleic acids include, but are not limited to, selective oligonucleotide hybridization, selective amplification, or selective primer extension. For example, oligonucleotide probes may be prepared in which the known polymorphic nucleotide is placed centrally and then hybridized to target DNA under conditions which permit hybridization only if a perfect match is found, e.g., see Saiki et al., Nature 324:163 (1986); Saiki et al., Proc. Natl Acad. Sci USA 86:6230 (1989); and Wallace et al., Nucl. Acids Res. 6:3543 (1979). Such specific oligonucleotide hybridization techniques may be used for the simultaneous detection of several nucleotide changes in different polymorphic regions of DNA. For example, oligonucleotides having nucleotide sequences of specific allelic variants are attached to a hybridizing membrane and this membrane is then hybridized with labeled sample nucleic acid. Analysis of the hybridization signal will then reveal the identity of the nucleotides of the sample nucleic acid. Alternatively unlabeled sample nucleic acid may be immobilized and contacted with labeled oligonucleotides that hybridize selectively with specific allelic variants.

Real-time pyrophosphate DNA sequencing is yet another approach to determine nucleotide sequence identity; see, for example, Alderborn et al., Genome Research, 10(8):1249-1258 (2000). Additional methods include, for example, PCR amplification in combination with denaturing high performance liquid chromatography (dHPLC); see, for example, Underhill et al., Genome Research, 7(10):996-1005 (1997).

In some embodiments, any of a variety of sequencing reactions known in the art can be used to directly sequence at least a portion of normalized and amplified DNA. Exemplary sequencing reactions include those based on techniques developed by Maxam and Gilbert, Proc. Natl. Acad. Sci USA, 74:560 (1977) or Sanger, Proc. Nat. Acad. Sci 74:5463 (1977). It is also contemplated that any of a variety of automated sequencing procedures may be utilized when performing the subject assays, e.g., see Venter et al., Science, 291:1304-1351 (2001); Lander et al., Nature, 409:860-921 (2001), including sequencing by mass spectrometry, e.g., see U.S. Pat. No. 5,547,835 and PCT Patent Publication No. WO 94/16101 and WO 94/21822; U.S. Pat. No. 5,605,798 and PCT Patent Application No. PCT/US96/03651; Cohen et al., Adv. Chromatogr. 36:127-162 (1996); and Griffin et al., Appl. Biochem. Biotechnol. 38:147-159 (1993). It will be evident to one skilled in the art that, for some embodiments, the occurrence of only one, two or three of the nucleic acid bases need be determined in the sequencing reaction. Yet other sequencing methods are disclosed, e.g., in U.S. Pat. Nos. 5,580,732; 5,571,676; 4,863,849; 5,302,509; PCT Patent Application Nos. WO 91/06678 and WO 93/21340; Canard et al., Gene 148:1-6 (1994); Metzker et al., Nucleic Acids Research 22:4259-4267 (1994) and U.S. Pat. Nos. 5,740,341 and 6,306,597. Particular sequencing methodologies that may benefit from the normalization methods described here include cyclic reversible termination and sequencing by ligation. Particular applications to which the various sequencing methodologies may be applied to include de novo genome sequencing, RNA-seq, and genome-wide profiling of epigenetic marks and chromatin structure (ChIP-seq; methyl-seq; DNAse-seq).

In some embodiments of the invention, the normalization methodologies described above (i.e., minimization of high copy number variation across samples or within a sample) can be incorporated into various stages of NGS sequencing platforms. For example, common adaptor sequences to be ligated to randomly fragmented DNA may be designed to incorporate uniquely identifying polynucleotides sequences (barcodes) and to comprise a nucleic acid sequence capable of hybridizing to a capture moiety. Normalization control can then be affected in pooled samples by controlling or equilibrating the amount of sample-specific capture moiety. In another example, clonal amplification of template (e.g., emulsion PCR) DNA may include the use of adaptors/primers comprising tag sequences that will be correspondingly incorporated into amplified molecules. Normalization can then follow the clonal amplification.

It will appreciated that a target need not necessarily be amplified prior to sequencing. Single molecule templates can be prepared for sequencing reactions. See, for example, Harris et al., Science, 2008, 320:106-109. For example, spatially distributed individual primer molecules may be covalently attached to a solid support. Nucleic acid targets may be randomly fragmented into approximately 200-250 base pair pieces. Capture tags may be attached to the fragment targets, as described above, wherein the tags comprise an identifying feature, a nucleotide sequence complementary to a capture moiety, and a nucleotide sequence complementary to the spatially distributed individual primer molecules bound to the solid support. The identifying feature, nucleotide sequence complementary to the capture moiety and the nucleotide sequence complementary to the immobilized primers may be separate, overlap, or be one in the same. Following the normalization protocol described above and dissociation of the tagged targets from the capture moieties, the normalized targets can be hybridized to the immobilized primers. A DNA polymerase is added to bind to the immobilized primed template configuration to initiate an NGS sequencing reaction. Various configurations of this approach (e.g., the normalized targets are covalently attached to and spatially distributed on the solid support) have been described.

Kits

In some embodiments, the present disclosure provides kits comprising materials useful for the normalization of biological targets according to methods described herein. The inventive kits may be used by diagnostic laboratories, experimental laboratories, or practitioners.

Materials and reagents useful for the normalization and eventual sequencing of biological targets according to the present disclosure may be assembled together in a kit. In some embodiments, an inventive kit comprises capture tags (or primers capable of incorporating the same into amplified targets), capture moieties, solid supports, and optionally, universal probes, reverse transcription and/or amplification reaction reagents. In some embodiments, the amount of capture moieties included may be optimized to normalize target copy number with respect to a particular sequencing platform, i.e., the amount of capture moiety included may be less than the maximum recommended initial target copy number for a particular sequencing technique. In some embodiments, a kit comprises reagents which render the procedure specific. Thus, a kit may be intended to be used for selection, normalization and sequencing of a particular subset of targets. A kit intended to be used for multiplex sequencing of a plurality of pooled targets from different samples, as described herein, comprises tags or capture moieties with an identifying feature (e.g., unique nucleic acid sequence) that allows the source of the targets to be identified and correlated with the targets isolated from that sample. A kit may comprise multiple tags, each with a different unique identifying feature.

Suitable reverse transcription/amplification reaction reagents that can be included in an inventive kit include, for example, one or more of: buffers; enzymes having reverse transcriptase and/or polymerase activity; enzyme cofactors such as magnesium or manganese; salts; nicotinamide adenide dinuclease (NAD); and deoxynucleoside triphosphates (dNTPs) such as, for example, deoxyadenosine triphosphate; deoxyguanosine triphosphate, deoxycytidine triphosphate and deoxythymidine triphosphate, biotinylated dNTPs, suitable for carrying out the amplification reactions.

Depending on the procedure, the kit may further comprise one or more of: wash buffers and/or reagents, hybridization buffers and/or reagents, labeling buffers and/or reagents, and detection means. The buffers and/or reagents included in a kit are preferably optimized for the particular amplification/detection technique for which the kit is intended. Protocols for using these buffers and reagents for performing different steps of the procedure may also be included in the kit.

Furthermore, the kits may be provided with an internal control as a check on the amplification procedure and to prevent occurrence of false negative test results due to failures in the amplification procedure. An optimal control sequence is selected in such a way that it will not compete with the target nucleic acid sequence in the amplification reaction (as described above).

Kits may also contain reagents for the isolation of nucleic acids from biological specimens prior to amplification and/or for nucleic acid extraction or the purification or separation of the same.

The reagents may be supplied in a solid (e.g., lyophilized) or liquid form. The kits of the present disclosure optionally comprise different containers (e.g., vial, ampoule, test tube, flask or bottle) for each individual buffer and/or reagent. Each component will generally be suitable as aliquoted in its respective container or provided in a concentrated form. Other containers suitable for conducting certain steps of the amplification/detection assay may also be provided. The individual containers of the kit are preferably maintained in close confinement for commercial sale.

The kit may also comprise instructions for using the kit according to one or more methods of the present disclosure, e.g., instructions for processing the biological sample, extracting nucleic acid molecules, and/or performing the test; instructions for interpreting the results as well as a notice in the form prescribed by a governmental agency (e.g., FDA) regulating the manufacture, use or sale of pharmaceuticals or biological products.

Embodiments of the invention are further defined by reference to the following examples.

EXAMPLES

Example 1—Capture Moieties Bound to Solid Substrate

A cDNA library is prepared from a selected cell type or tissue in each of N different subjects, wherein N can be any number. The libraries are then randomly fragmented. Each set of library fragments is then terminated with a DNA capture tag comprising a unique, single-stranded binding/hybridization ("hyb") domain. Each library has its own tag with a nucleic acid sequence unique to that sample, as shown in FIG. 1 (Library 1 with hyb-1; Library 2 with hyb-2; Library N with hyb-N, etc.). Library 1 comprises six tagged targets, Library 2 comprises 3 tagged targets, and Library N comprise five tagged targets. Exemplary tag sequences are show below in Table 1:

TABLE 1

| Name | Sequence (5'-3') | Length | SEQ ID NO. |
|---|---|---|---|
| c1 | TTTTTTTTTTTTCGGCGAAACTCCGCACCGCCACG | 35 | 1 |
| c2 | TTTTTTTTTTTCCCAGGACGGCGCTGGCACGTTGA | 35 | 2 |
| c3 | TTTTTTTTTTCATGAGCAAGCTGCAGCTGCGCGCG | 35 | 3 |
| c4 | TTTTTTTTTTAAAGCGGGCGGCGATCGCGAATGTC | 35 | 4 |
| c5 | TTTTTTTTTTGATGGTGATCCCGCGCGTGCCGAAA | 35 | 5 |
| c6 | TTTTTTTTTTTCGAATTCTCGGTGTCCGCGGGCGA | 35 | 6 |
| c7 | TTTTTTTTTTATCTTGCGCGGCAGCTCGTCGACCG | 35 | 7 |

TABLE 1-continued

| Name | Sequence (5'-3') | Length | SEQ ID NO. |
|---|---|---|---|
| c8 | TTTTTTTTTTCCGGTCGATCGTGGTGTTCGCGGCT | 35 | 8 |
| c9 | TTTTTTTTTTGTGCGCCCGAGATCGGTATCGCCG | 35 | 9 |
| c10 | TTTTTTTTTTCGACGCGGGCTTGGTACGTTTGGCG | 35 | 10 |

These tags have sufficient length such that they are stable and able to hybridize with a complementary sequence under standard hybridization conditions (temperature, pH, salt, etc.), yet also dissociate in a controlled and reproducible manner. For example, the tags may have a melting temperature of Tm~75° C. at 50 mM sodium chloride, such that hybridization and capture is accomplished below the Tm at 70° C. at 50 mM sodium chloride. Contamination can then be removed. The target fragments are then optionally released either by (1) increasing the temperature to 80° C., or by (2) decreasing the sodium chloride to 20 mM. These tags are also sufficiently unique to ensure selectivity between samples. Thus, the samples are pooled after tagging.

Oligonucleotide capture moieties comprising a DNA sequence complementary to the capture tag sequence are bound to solid substrates through EDC/NHS chemistry; for example, paramagnetic micron-scale beads approximately 100 ηm to 1 μm in diameter. As each target from a given sample is tagged with the same unique identifying feature, the amount of capture moieties is selected for each sample and bound to the solid substrate in a precise stoichiometry. The amount of capture moiety is equivalent for all of the samples and is less than the most abundant targets in any one of the samples. For example, as shown in FIG. 1, four capture moieties are attached that are complementary to the capture tag sequence of Library 1, four capture moieties are attached that are complementary to the capture tag sequence of Library 2; four capture moieties are attached that are complementary to the capture tag sequence of Library N, etc. Thus, the stoichiometrically normalized capture moieties function to limit the pull-down of over-abundant libraries.

The pooled, tag-terminated libraries are mixed with capture moieties under conditions suitable for binding and hybridization, permitting the complementary tag/moiety pairs to bind up to the stoichiometric limit of the capture moieties for a given sample. As shown in FIG. 1, four targets from Library 1 are pulled down, four targets from Library 2 are pulled down, and four targets from Library N are pulled down. Thus, over-abundant targets that exceed the available binding capacity of the capture moieties remain in the pooled solution. As exemplified in FIG. 1, two targets of Library 1 and one target of Library N are not captured and, therefore, not subsequently processed for library sequencing.

After addition of the tagged targets, the substrate is washed under stringent conditions to preserve hybridization yet remove all tagged targets lacking a capture moiety binding partner on the solid substrate. After washing, the solid substrate is subjected to conditions that cause dissociation of the normalized targets. Released targets are then available for NGS sequencing protocols, which elucidate the sequence of both the targets and their tags, Thus, the sequenced targets/tags can be correlated with their original samples.

Example 2—Normalization in Solution

Direct attachment of stoichiometrically normalized capture moieties to a solid substrate is not ideal for every embodiment of the invention. Such attachment requires new fabrication of the substrate/capture moiety combination whenever different or additional samples are processed, or when a different binding capacity is required. It is also difficult to control the exact stoichiometry of capture moiety oligonucleotides on solid surfaces due to surface chemistry variability. Moreover, any surface capture variation (e.g., from substrate, capture moiety oligonucleotides or chemical processing) directly impacts binding capacity, possibly in a probe-specific manner, which can dramatically impact normalization.

Thus, quality control of normalization is optimized when the stoichiometrically normalized capture moieties are bound to the targets in solution and subsequently captured on a solid support via a universal probe bound to the solid surface. There are only two requirements in such embodiments: (1) the universal probe must comprise a feature (e.g., complementary oligonucleotide sequence) capable of binding every capture moiety regardless of sample (e.g., a sequence that hybridizes universally to the capture moieties); and (2) the universal probes must be present in excess of any of the targets in any of the samples. In other words, the exact binding capacity of the solid substrate is immaterial as long at it is greater (e.g., 2×, 3×, 4×, 5×, etc.) than the output of the library.

Figure 2A:
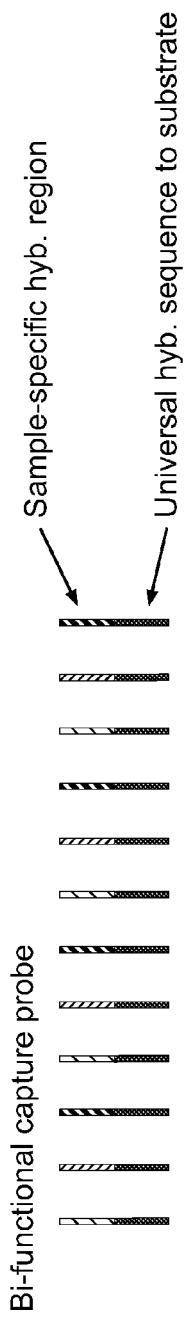
FIG. 2 presents an embodiment of the invention in which normalization control is achieved in solution through bi-functional capture moieties comprising a first part that binds (e.g., hybridizes) to previously tagged library fragments (not shown) and a second part that hybridizes to universal capture probes (e.g., each an oligonucleotide comprising a sequence complementary to the second part of the capture moiety).
Figure 2A:
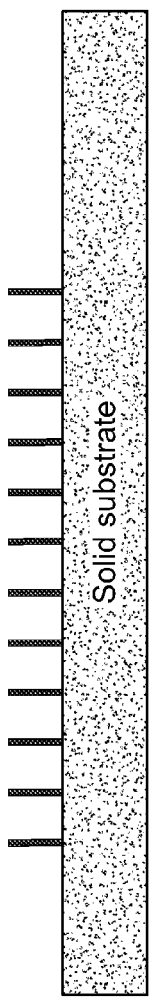
Figure 2A:
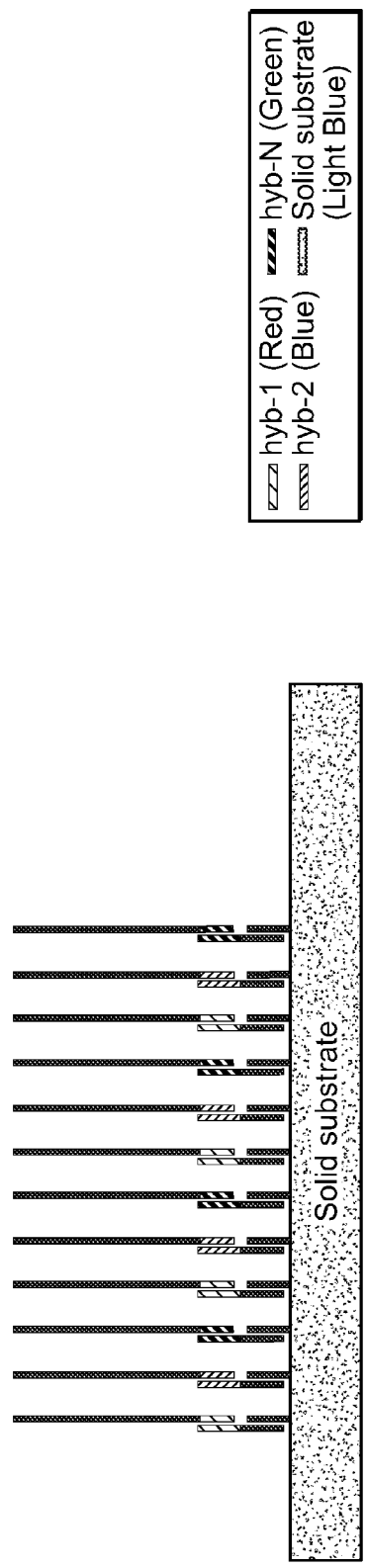

As shown in FIG. 2A, a bi-functional capture moiety oligonucleotide is utilized, comprising one part with a sample-specific tag hybridization sequence and a second part with a hybridization sequence complementary to the universal probes. Samples are isolated and targets tagged with sample-identifying features, as above. The samples are then pooled. A stoichiometrically predetermined amount of the sample-specific bi-functional capture moiety oligonucleotides is mixed with the pooled library fragments. The amount is equivalent across all samples. Because the bi-functional capture moiety oligonucleotides are sample-specific, the amount added per sample caps the number of tagged targets isolated from that sample. In other words, the capture moieties control the total binding capacity of the library fragments, which occurs independent of the binding capacity of the solid support. Unbound fragments are not captured and are washed away as above.

Figure 2B:
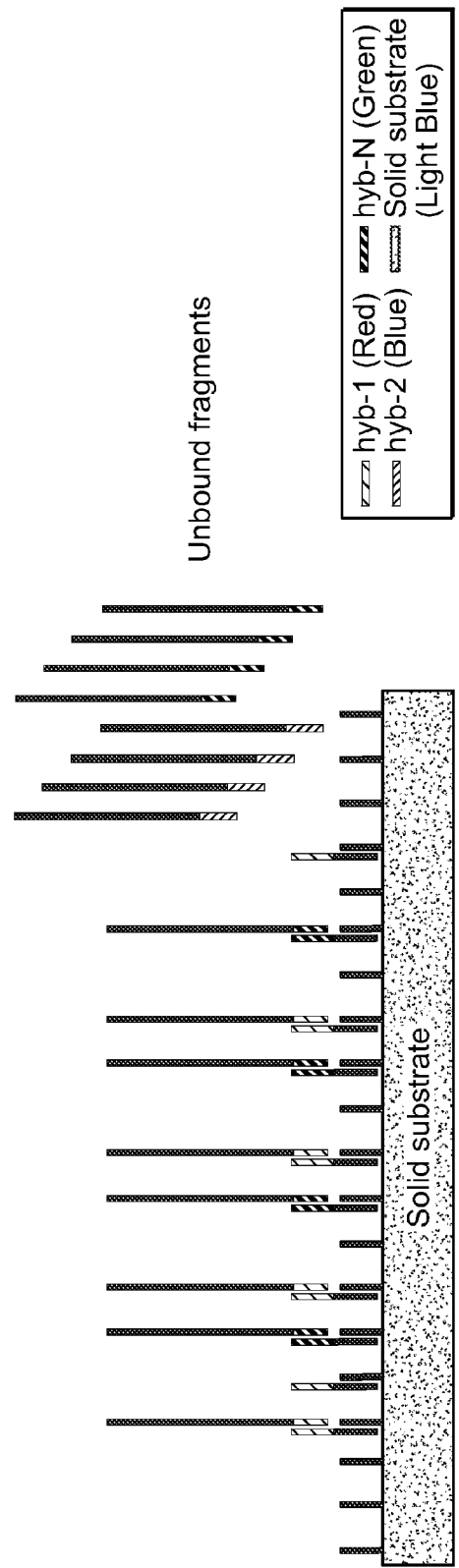

Using bi-functional capture moieties renders the normalization protocols described herein exceptionally customizable. For example, where multiple samples are obtained and targets from those samples pooled, it may be necessary to normalize targets from only one of the samples, two of the samples, etc. As shown in FIG. 2B, sample-derived libraries described as "red", "blue", "green" and "black" may be tagged in a sample-specific manner (e.g., "red" tags, "blue" tags, etc.) and pooled into a single reaction mixture. Normalization protocols can be designed to leave out the blue library by not including bi-functional capture probes capable of binding the "blue" tags. Thus, only specific quantities of "red", "green" and "black" capture moieties need be included, such that any library targets in excess of the quantities added will not be bound by the bi-functional capture moiety and, correspondingly, the substrate. Libraries with fewer targets (e.g., fragments) than capture moieties allow for full collection of those targets, while any extra bi-functional capture moieties are vacant with respect to the target but bound to the universal probe present in excess on the solid support.

Example 3—Protein-Based Normalization

As shown in FIG. 3, embodiments of the invention are not limited to capture by nucleic acids. Amino acids can be substituted to perform the same roles as nucleic acids in the previous examples. In FIG. 3, streptavidin is bound to a solid support to serve as a universal probe. For example, streptavidin can be cross-linked to beaded agarose, which is commercially available. The capture moiety is biotinylated antibody capable of binding to the immunoglobulin-binding domains of staphylococcal protein A or the serum albumin-binding regions of streptococcal protein G. Library fragments derived from different samples can be tagged in a sample-specific manner with either protein A or protein G, pooled, and then incubated with stoichiometrically normalized amounts of biotinylated antibody capture moiety. Protein tagging of nucleic acids may be performed by methods well-known to those of skill in the art, such as EDC chemistry. Methods of conjugating protein G to oligonucleotides have been described previously (see, e.g., U.S. Publication No. 2010/0203653).

EQUIVALENTS

Those skilled in the art will recognize, or be able to ascertain using no more than routine experimentation, many equivalents to the specific embodiments of the inventions described herein. The scope of the present disclosure is not intended to be limited to the scope of the above description, but rather is as set forth in the following claims.

All references cited herein are incorporated by reference in their entirety.

What is claimed is:

1. A method of normalizing biological samples, the method comprising:
   obtaining multiple samples, each sample comprising a plurality of targets;
   attaching capture tags to substantially all of the targets in a given sample, wherein each capture tag comprises an identifying feature and a capture moiety-binding domain, both of which are unique to the sample to which it is added;
   pooling the samples;
   adding an amount of a capture moiety for each sample, wherein each capture moiety is specific for the capture moiety-binding domain of the capture tag utilized in a given sample, and wherein the total amount of each sample-specific capture moiety
   a. is equivalent across all samples, and
   b. is less than at least the most abundant target in any one of the samples; and capturing the targets.

2. The method of claim 1, wherein the targets comprise nucleic acid sequences.

3. The method of claim 2, wherein the nucleic acid is DNA.

4. The method of claim 3, wherein the targets comprise members of a DNA library.

5. The method of claim 2, wherein the targets are fragmented prior to attaching the capture tags.

6. The method of claim 1, wherein the capture tags are oligonucleotides.

7. The method of claim 6, wherein the capture tags are deoxyribonucleotides.

8. The method of claim 7, wherein the capture tags are ligated to the target.

9. The method of claim 7, wherein the capture tags are at least partially single-stranded.

10. The method of claim 6, wherein the capture tags further comprise base modifications.

11. The method of claim 6, wherein the capture moieties are oligonucleotides.

12. The method of claim 11, wherein the capture moiety oligonucleotides comprise a sequence complementary to the oligonucleotide capture tags attached to the targets.

13. The method of claim 11, wherein both the capture moiety oligonucleotides and the capture tag oligonucleotides are DNA.

14. The method of claim 1, wherein the identifying feature is a specified DNA sequence within the capture tag.

15. The method of claim 1, wherein the capture tags are 15-35 base pairs in length.

16. The method of claim 1, wherein capturing the targets comprises affixing the capture moieties to a solid support.

17. The method of claim 16, wherein the solid support is a paramagnetic micron bead.

18. The method of claim 16, wherein the solid support is 100 nm by 1 μm by 1 μm in dimension.

19. The method of claim 16, wherein the capture moieties are covalently attached to the solid support.

20. The method of claim 19, wherein the capture moieties are covalent attached through amine coupling or azide-alkyne cycloaddition.

21. The method of claim 16, wherein the capture moieties comprise a first part that binds to the capture tags and a second part that binds to universal probes attached to the solid support.

22. The method of claim 21, wherein the probes are oligonucleotides.

23. The method of claim 22, wherein each oligonucleotide probe comprises an identical nucleotide sequence capable of hybridizing to a corresponding sequence found in each capture moiety.

24. The method of claim 23, wherein the oligonucleotides are DNA.

25. The method of claim 21, wherein the parts are terminal.

26. The method of claim 21, wherein the ratio of capture moieties to probes is from 1:2 to 1:100.

27. The method of claim 21, wherein the probes are streptavidin, the capture moieties are biotinylated antibodies, and the capture tags attached to the targets are proteins bound by the antibodies.

28. The method of claim 1, further comprising removing the capture tag from the target by exposure to non-hybridizing conditions, photocleavage, chemical cleavage, or restriction endonucleases.

29. The method of claim 1, further comprising detaching the targets from the capture moieties.

30. The method of claim 29, wherein detachment is effected by altering hybridization conditions.

31. The method of claim 1, further comprising sequencing the captured targets.

32. The method of claim 31, wherein the targets are polynucleotides.

* * * * *